United States Patent [19]

Nakamura

[11] Patent Number: 4,823,803

[45] Date of Patent: Apr. 25, 1989

[54] HALITOSIS DETECTOR DEVICE

[75] Inventor: Katunori Nakamura, Iwatsuki, Japan

[73] Assignee: Winners Japan Company Limited, Tokyo, Japan

[21] Appl. No.: 172,595

[22] Filed: Mar. 24, 1988

[30] Foreign Application Priority Data

Jul. 31, 1987 [JP] Japan .................................. 62-190159

[51] Int. Cl.$^4$ .............................................. A61B 10/00
[52] U.S. Cl. ..................................... 128/717; 128/719
[58] Field of Search ........................ 128/717, 719, 736

[56] References Cited

U.S. PATENT DOCUMENTS

| | | | |
|---|---|---|---|
| 1,525,631 | 2/1925 | White .................................. | 128/717 |
| 3,713,434 | 1/1973 | Leslie .................................. | 128/717 |
| 4,151,831 | 5/1977 | Lester .................................. | 128/736 |
| 4,334,540 | 6/1982 | Poeti et al. ....................... | 128/717 X |
| 4,656,008 | 4/1987 | Gump .................................. | 128/719 X |
| 4,749,553 | 6/1988 | Lopez et al. ..................... | 125/719 X |
| 4,756,670 | 7/1988 | Arai .................................... | 128/719 X |

Primary Examiner—Edward M. Coven
Attorney, Agent, or Firm—Martin Smolowitz

[57] ABSTRACT

A device for testing human exhalation for halitosis, comprising a chamber having an air inlet through which the exhalation to be tested is admitted into the chamber and an air outlet through which the exhalation tested is discharged from the chamber, a sensor element located in the chamber and, when heated to a first temperature, sensitive to malodorant gases of predetermined chemical compositions for producing a signal variable with the detected concentration of the malodorant gases, a heater element which, when electrically activated, is operative to heat the sensor element selectively to the first temperature or a second temperature, the second temperature being higher than the first temperature and being selected to regenerate the sensing means, a control circuit responsive to the signal from the sensor element for determining the degree of malodorousness on the basis of the signal and producing a signal representative of the degree of malodorousness determined, and a display screen or a plurality of indicators responsive to the signal from the control circuit for displaying information relating to the degree of malodorousness represented by the signal from the control circuit.

4 Claims, 13 Drawing Sheets

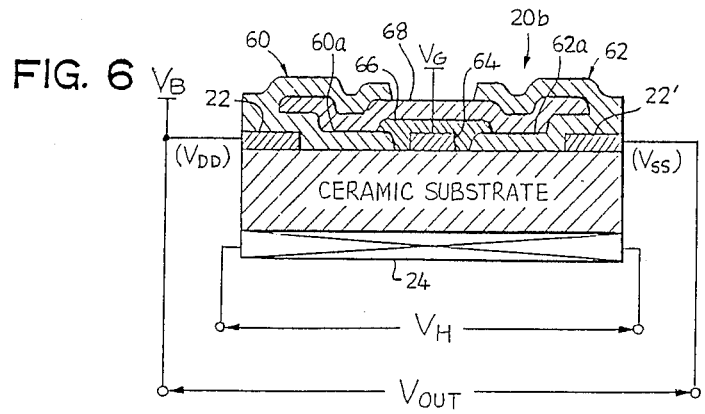
FIG. 6
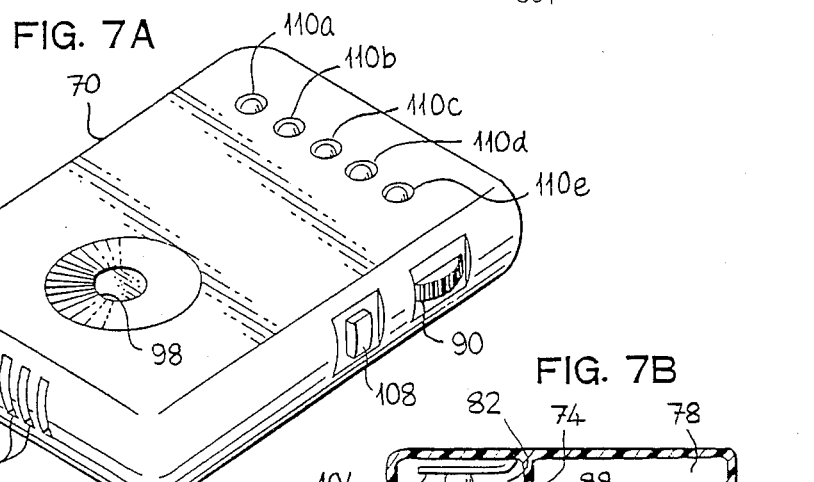
FIG. 7A
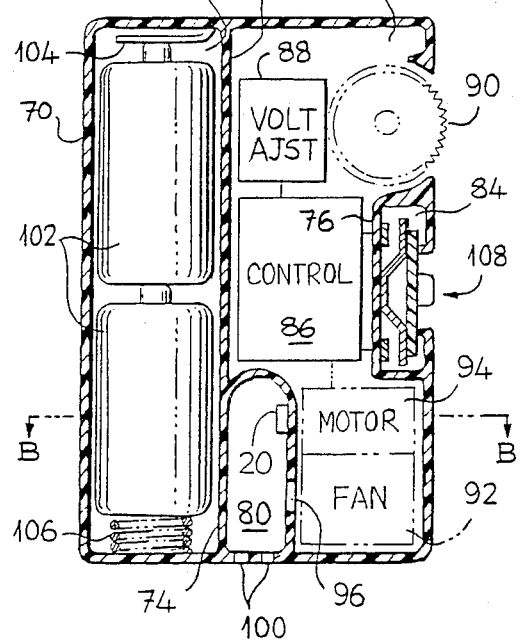
FIG. 7B
FIG. 7C

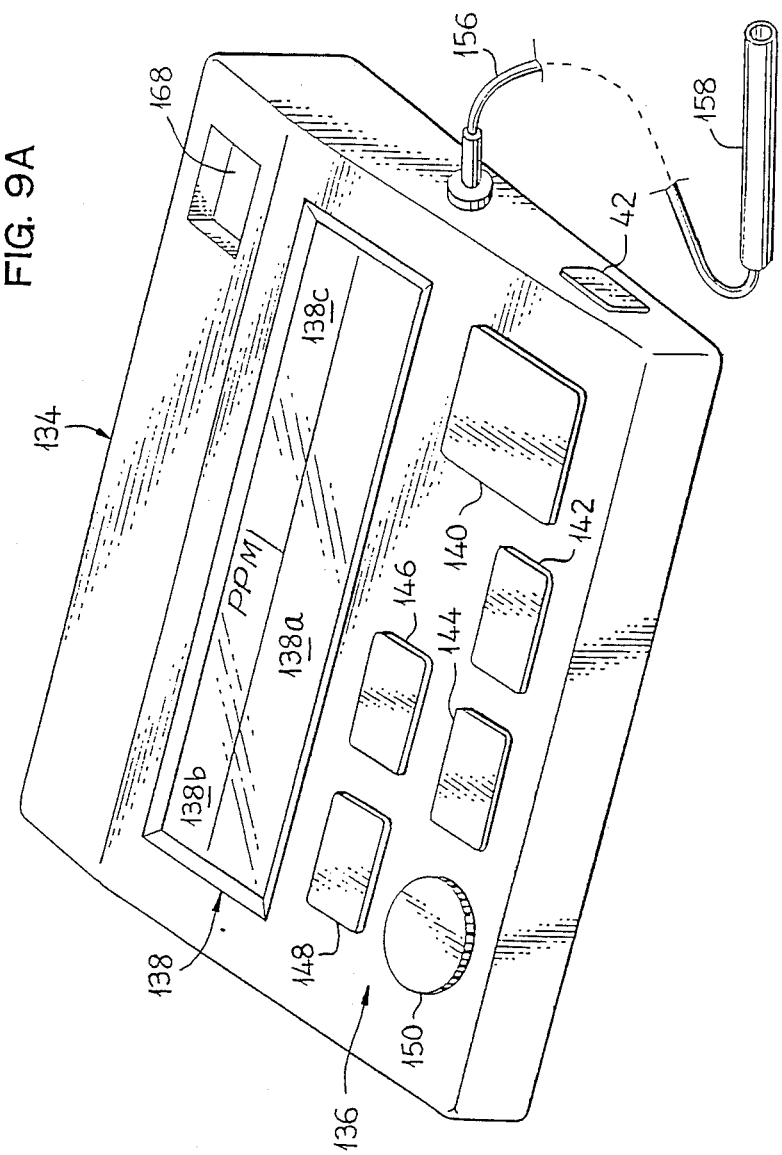

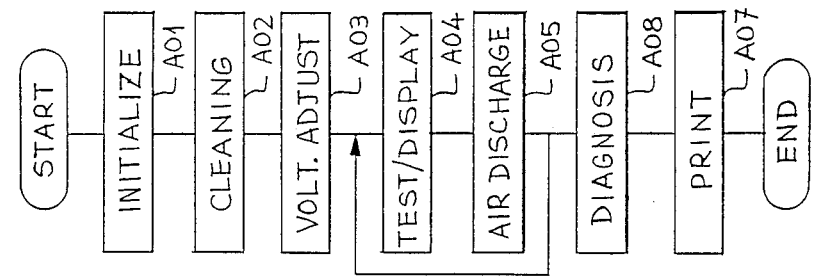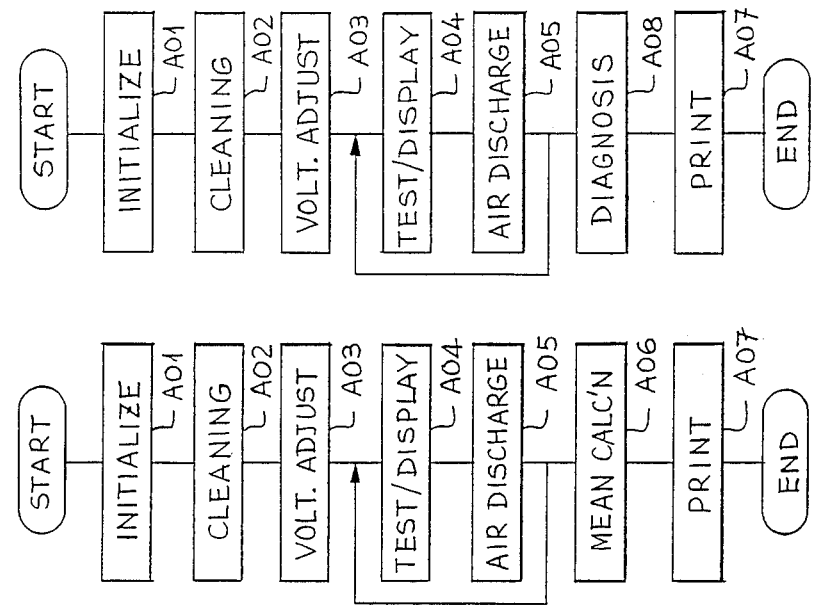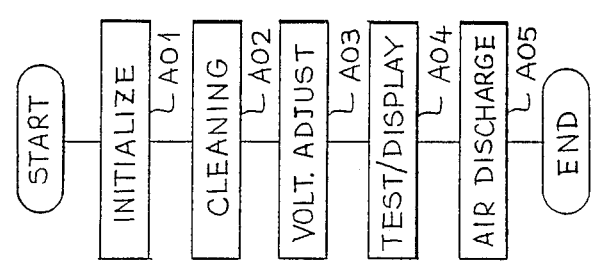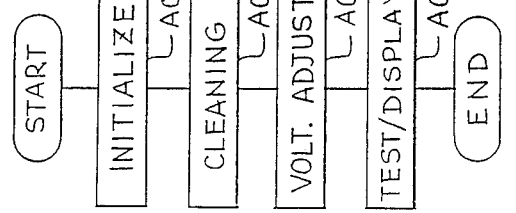

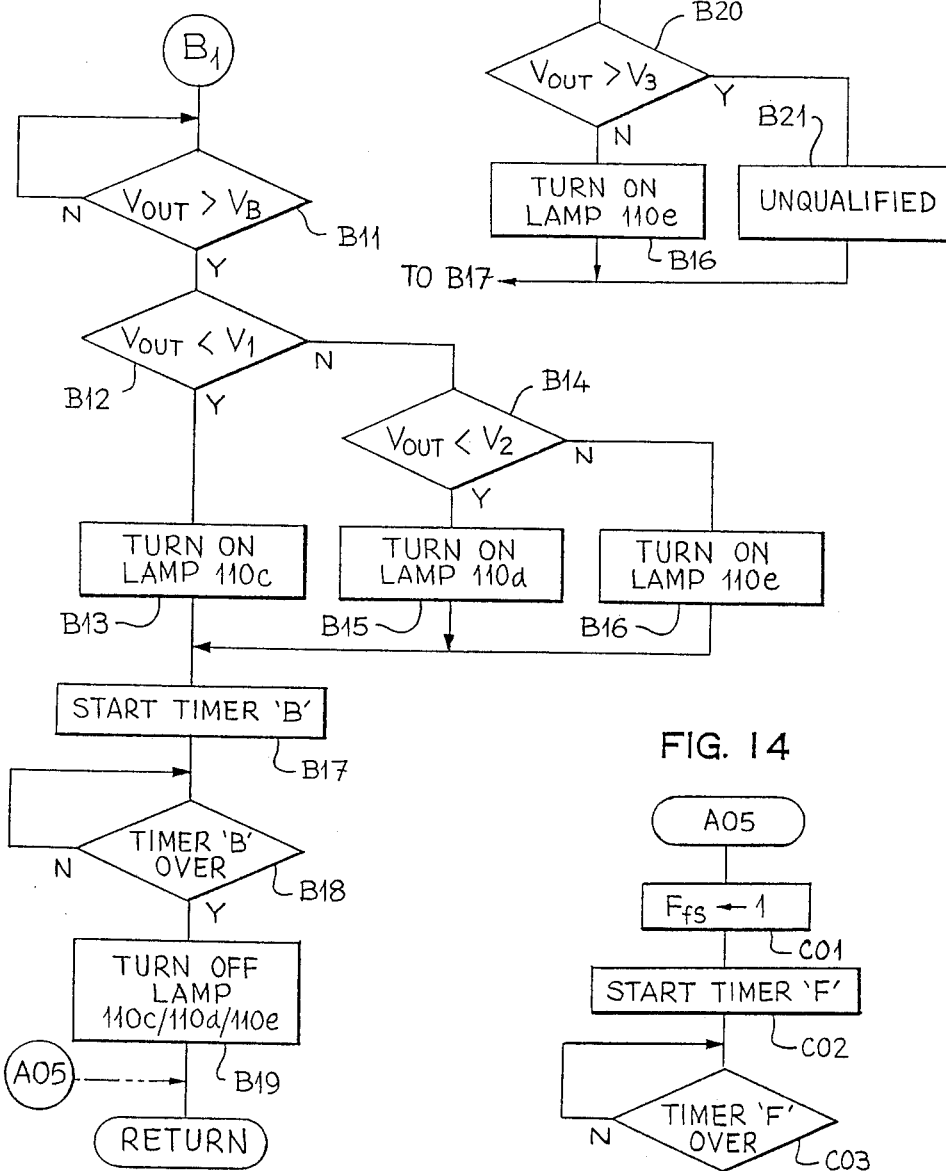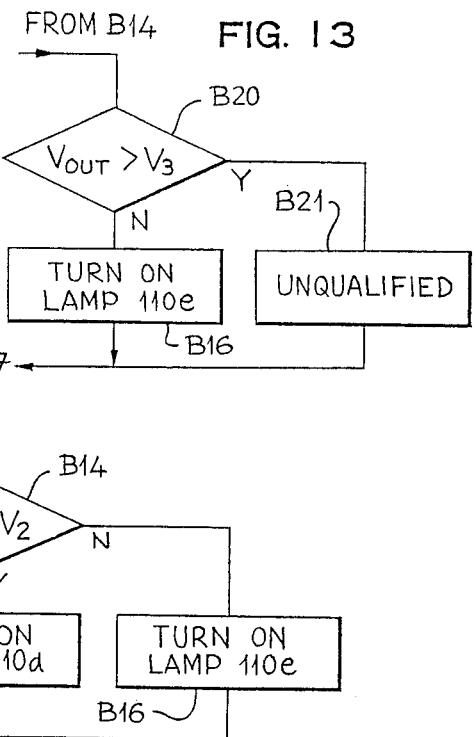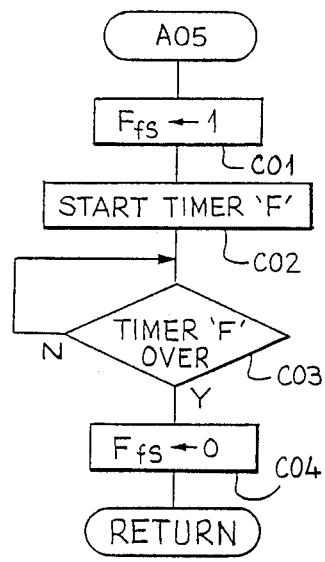

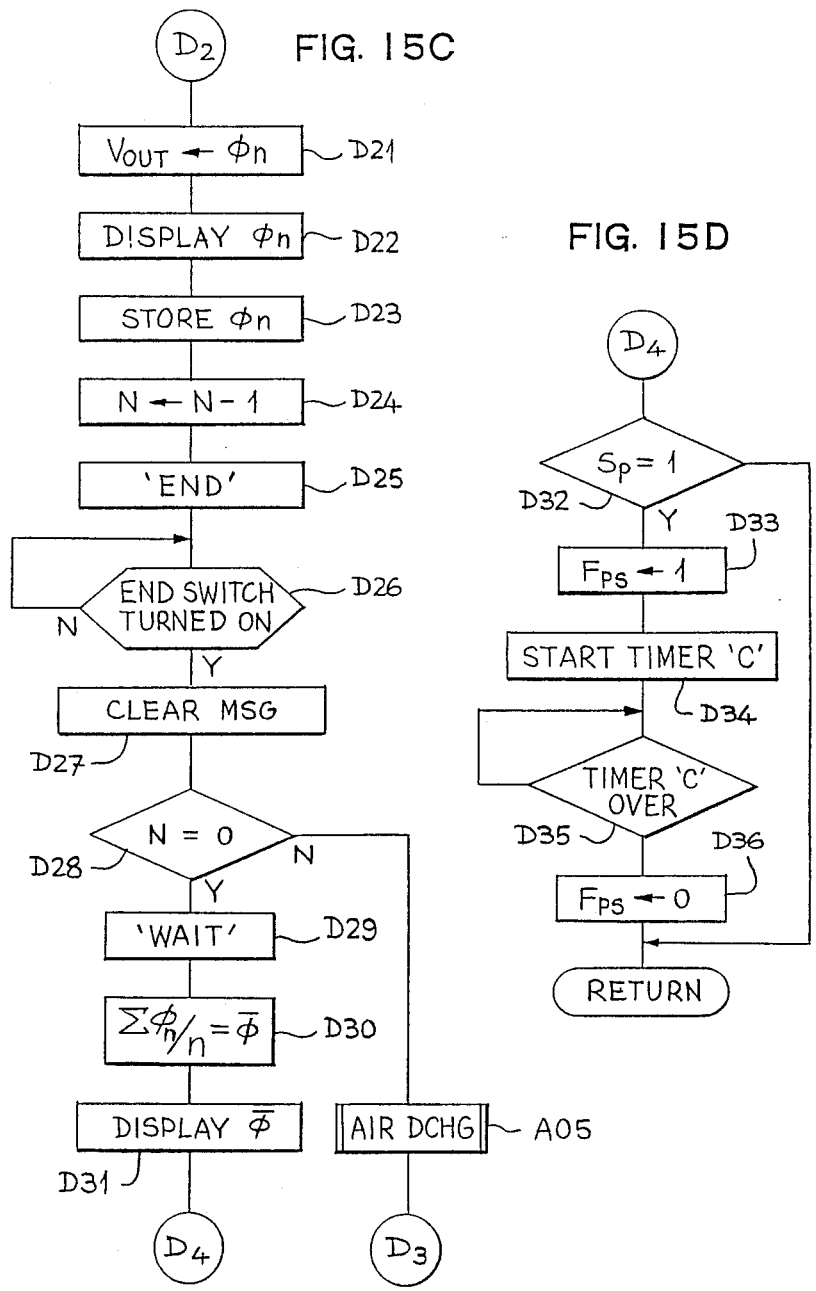

HALITOSIS DETECTOR DEVICE

The present invention relates to a halitosis detector device for detecting malodorants in human exhalations and, more particularly, to a halitosis detector device capable of detecting human halitosis and/or quantitatively determining the degree of malodorousness of human exhalation. The present invention further relates to a method of detecting halitosis and/or quantitatively determining the degree of malodorousness of human exhalation and to a method of diagnosing a case suspected of ozostomnia.

Only organoleptic tests relying on human olefactory senses are used for the detection of oral malodors and determination of the degree of halitosis or malodorousness of human exhalations. Such organoleptic tests are conducted ordinarily by a panel which is organized by several trained specialists to cooperatively estimate the degrees of halitosis simply by having recourse to the sense of smell. The organoleptic tests by panelling are however ineffectual for the quantitation of the seriousness of halitosis, much less the concentrations of malodorants in the human exhalations.

Quantitative analysis of malodorants in human exhalations can be and has actually been conducted by gas chromatography typically using a flame photometer or a hydrogen flame ionization detector device. In the flame photometric gas chromatographic measurement of malodorants, the air breathed out by a subject or examined suspected of ozostomnia is directed toward an adsorbent material so that the chemical components of the breath are applied to the adsorbent material. The adsorbent material to which the malodorant gases which may be contained in the subject's exhalation has thus been exposed is combusted for the detection, identification and quantitation of the malodorant gases through measurement of the intensity of the illumination from the combustion of the gases. Such quantitative measurement of malodorants in human exhalations requires the use of a large-scaled, elaborate and accordingly expensive testing equipment which is not adapted for home or personal use or for use at a private dental clinic.

It is experimentally known that halitosis is caused by the presence of about twenty to hundred kinds of chemical substances contained in human breaths. Typical of these substances thus contributing to the production of human halitosis are hydrogen sulfide $H_2S$, dimethyl sulfide $(CH_3)_2S$, methyl mercaptan $CH_3SH$, and ethyl mercaptan $C_2H_5SH$. Hydrogen sulfide is generated from, for example, accumulation of dental plaque on the teeth and could be eliminated by constant cleaning of the oral cavity. Dimethyl sulfide is known to be absent in the breath of a normal breather and is detected only in the exhalation of a patient suffering from morbid ozostomnia, as has been observed by periodontists. Further contained in the breath of a patient suffering from morbid ozostomnia are methyl mercaptan and ethyl mercaptan each in an appreciable concentration as typical malodorants responsible for halitosis, also according to the periodontists.

These chemical substances contributing to production of human halitosis could be detected and quantitated through use of a known gas sensor sensitive to reducing gases of certain chemical compositions. Simple application of such a gas sensor for the detection and measurement of malodorants in human exhalations would however raise a problem in that not only the malodorant reducing gases of interest but also other chemical substances which are not contributive to production of halitosis may be detected and measured by the sensor.

It is, accordingly, an important object of the present invention to provide a portable-type halitosis detector device capable of easily and conveniently detecting human halitosis.

It is another important object of the present invention to provide a portable-type halitosis detector device capable of quantitatively determining the degree of malodorousness of human exhalations conveniently and yet reliably.

It is still another important object of the present invention to provide a portable-type halitosis detector device which is simple in construction, easy and economical to manufacture and use, and yet reliable in performance.

It is still another important object of the present invention to provide a handy, portable-type halitosis detector device which is adapted for home or personal use or for use at a private dental clinic.

It is still another important object of the present invention to provide a portable-type halitosis detector device which is sensitive specifically to the chemical gases contributing to production of halitosis.

It is still another important object of the present invention to provide a method of detecting halitosis and/or quantitatively determinating the degree of malodorousness of human exhalations.

It is, yet, still another important object of the present invention to provide a method of diagnosing a case suspected of ozostomnia.

In accordance with the present invention, there is provided a halitosis detector device for testing human exhalation for halitosis, comprising (a) a chamber having an air inlet through which the exhalation to be tested is to be admitted into said chamber and an air outlet through which the exhalation tested is to be discharged from the chamber, (b) sensing means located in the chamber and, when heated to a predetermined first temperature, sensitive to malodorant gases including those of predetermined chemical compositions for producing an electrical signal variable in magnitude with the detected concentration of the malodorant gases, (b) means which, when electrically activated, is operative to heat the sensing means selectively to the first temperature or a predetermined second temperature, the second temperature being higher than the first temperature and being selected to regenerate the sensing means, (c) control means responsive to the signal for determining the degree of malodorousness on the basis of the signal and producing an electric signal representative of the degree of malodorousness determined, and (d) display means responsive to the signal from the control means for displaying information relating to the degree of malodorousness determined by the signal from the control means.

The features and advantages of a halitosis detector device and a method according to the present invention will be more clearly appreciated from the following description taken in conjunction with the accompanying drawings in which like reference numerals designate similar or corresponding units, members and elements and in which:

FIG. 6 is a longitudinal sectional view showing the detailed construction of a typical example of a thermally activated thin-film adsorption-effect transistor used as a sensor element in the halitosis detector device shown in FIG. 2B or 3B;

FIG. 7A is a perspective view showing the external construction of a preferred embodiment of a halitosis detector device incorporating the arrangement illustrated in FIG. 2A;

FIG. 7B is a plan view showing, partly in section, the internal construction of the halitosis detector device illustrated in FIG. 7A;

FIG. 7C is a cross sectional view taken along line C—C in each of FIGS. 7A and 7B;

FIG. 9A is a perspective view showing the external construction of a preferred embodiment of a halitosis detector device incorporating the arrangement illustrated in FIG. 3A;

FIGS. 11A, 11B, 11C and 11D are flowcharts respectively showing some preferred examples of the main routine program which may be executed by the central processing unit incorporated in the control circuit of a halitosis detector device embodying the present invention;

FIGS. 12A and 12B are flowcharts showing the details of the routine program illustrated in FIG. 11A as applied to the device of FIGS. 7A to 7C;

FIG. 13 is a flowchart showing steps which may be included additionally in the routine program illustrated in FIGS. 12A and 12B;

FIG. 14 is a flowchart showing the details of a forced air discharge subroutine which is included in the routine program illustrated in FIG. 11B in addition to the routine program of FIG. 11A;

FIGS. 15A, 15B, 15C and 15D are flowcharts showing the details of the routine program illustrated in FIG. 11C as applied to the device of FIGS. 9A and 9B;

Figure 1:
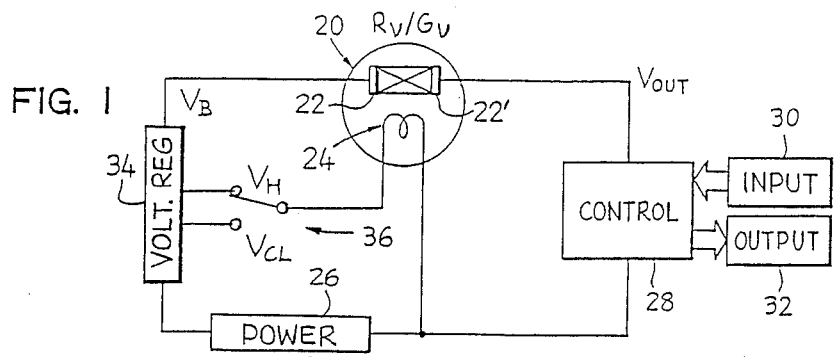
FIG. 1 is a diagram schematically showing the general circuit arrangement of a halitosis detector device according to the present invention.

Referring to FIG. 1 of the drawings, a halitosis detector device according to the present invention basically comprises a sensor unit 20 having a pair of electrodes 22 and 22' and a heater element 24 adapted to generate heat when electrically activated. The sensor unit 20 is of the type which is sensitive to anion-adsorptive reducing gases of prescribed chemical compositions and which is variable in resistance $R_v$ or conductance $G_v$ when thermally activated. The chemical substances to which the sensor unit 20 is thus sensitive are specifically those contributive to production of halitosis and include hydrogen sulfide $H_2S$, dimethyl sulfide $(CH_3)_2S$, methyl mercaptan $CH_3SH$, and ethyl mercaptan $C_2H_5SH$, as has been noted. When the sensor unit 20 is thermally activated with the heater element 24 electrically energized and is exposed to an ambient containing any one or more of such malodorant gases, the resistance $R_v$ or conductance $G_v$ between the electrodes 22 and 22' continuously varies with the total concentration of the malodorant substances in the ambient.

In the schematic circuit arrangement shown in FIG. 1, the heater element 24 is connected across a constant-voltage power supply circuit 26, while the sensor unit 20 per se is connected across the power supply circuit 26 through a control circuit 28. The control circuit 28 is thus responsive to a variable differential voltage produced between the electrodes 22 and 22' as a result of the variation in the resistance $R_v$ or conductance $G_v$ of the sensor unit 20. The control circuit 28 is coupled to input and output networks 30 and 32 through which various instruction and data signals may be supplied to and from the control circuit 28 during operation of the detector device.

As will be described in more detail, a predetermined bias voltage $V_B$ is constantly applied between the electrodes 22 and 22' through a suitable constant voltage generator circuit 34. The constant voltage generator circuit 34 has an input terminal connected to the power supply circuit 26 and an output terminal connected to one of the electrodes 22 and 22' of the sensor unit 20. When the sensor unit 20 is placed in an ambient containing malodorant gases, a signal voltage $V_{OUT}$ higher than the bias voltage $V_B$ and variable with the concentration of the detected malodorant reducing gases is thus produced between the electrodes 22 and 22'. The signal voltage $V_{OUT}$, which is thus indicative of the concentration of the detected malodorant reducing gases, is supplied to the control circuit 28. The voltage generator circuit 34 further has two output terminals connected to the heater element 24 across a two-position or two-state switch circuit 36 through which different fixed voltages $V_H$ and $V_{CL}$ are to be selectively supplied to the heater element 24. As will be described in more detail, the voltage $V_H$ is to be applied to the heater element 24 for the detection of malodorant gases and is herein referred to as heater voltage. On the other hand, the voltage $V_{CL}$ is to be used for the regeneration or "cleaning" of the sensor unit 20 which is contaminated by the combustion of the reducing gases after detection of the gases and is herein referred to as sensor cleaning voltage.

Figure 2A:
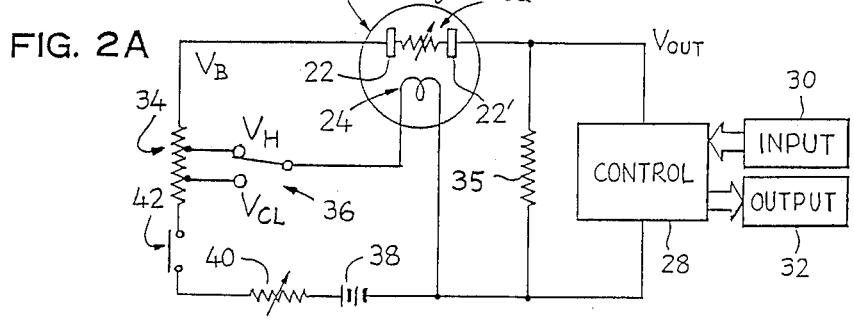
FIG. 2A is a diagram showing the circuit arrangement of a first preferred form of halitosis detector device basically arranged as shown in FIG. 1.

FIG. 2A shows the circuit arrangement of a first preferred form of halitosis detector device basically arranged as hereinbefore described with reference to FIG. 1. The sensor unit 20 of the detector device herein shown comprises a thermally activated metal-oxide semiconductor sensor element 20a having input and output ends coupled to the electrodes 22 and 22′, respectively. The sensor element 20a has a variable resistance $R_v$ which, when the associated heater element 24 is electrically activated by the heater voltage $V_B$, continuously varies with the total concentration of the reducing gases to which the sensor element 20a is exposed. Between the electrodes 22 and 22′ is thus produced a signal voltage $V_{OUT}$ higher than the fixed bias voltage $V_B$ and variable with the concentration of the detected reducing gases to which the sensor element 20a is subjected. The constant voltage generator circuit 34 is implemented by a variable resistor connected between the power supply circuit 26 and the sensor element 20a and having two taps connected across the switch circuit 36 to the heater element 24. The power supply circuit 26 per se is herein assumed to comprise a series combination of a d.c. power source 38, a voltage regulator implemented by a variable resistor 40 and a normally-open power supply switch 42. There is further shown a resistor 35 connected between the power supply circuit 26 and the output electrode 22′ of the sensor unit 20.

Figure 2B:
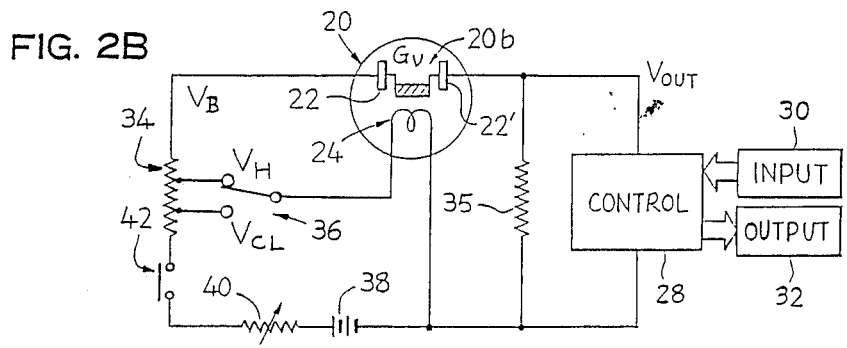
FIG. 2B is a diagram showing the circuit arrangement of a second preferred form of halitosis detector device basically arranged as shown in FIG. 1.

FIG. 2B shows the circuit arrangement of a second preferred form of halitosis detector device basically arranged as hereinbefore described with reference to FIG. 1. The sensor unit 20 of the detector device herein shown comprises a sensor element 20b implemented by a thermally activated thin-film adsorption-effect transistor (AET) having a current path connected between the electrodes 22 and 22′. The AET sensor element 20b has a variable conductance $G_v$ which, when the associated heater element 24 is electrically activated, continuously varies with the total concentration of the malodorous reducing gases to which the sensor element 20b is subjected. Between the electrodes 22 and 22′ of the sensor unit 20 is thus produced a signal voltage $V_{OUT}$ higher than the fixed bias voltage $V_B$ and variable with the concentration of the detected reducing gases to which the sensor element 20b is subjected. The constant voltage generator circuit 34 is also implemented by a variable resistor connected between the power supply circuit 26 and the sensor element 20a and having two taps connected across the switch circuit 36 to the heater element 24. The power supply circuit 26 comprises a series combination of a d.c. power source 38, a variable resistor 40 implementing a voltage regulator and a normally-open power supply switch 42.

Figure 3A:
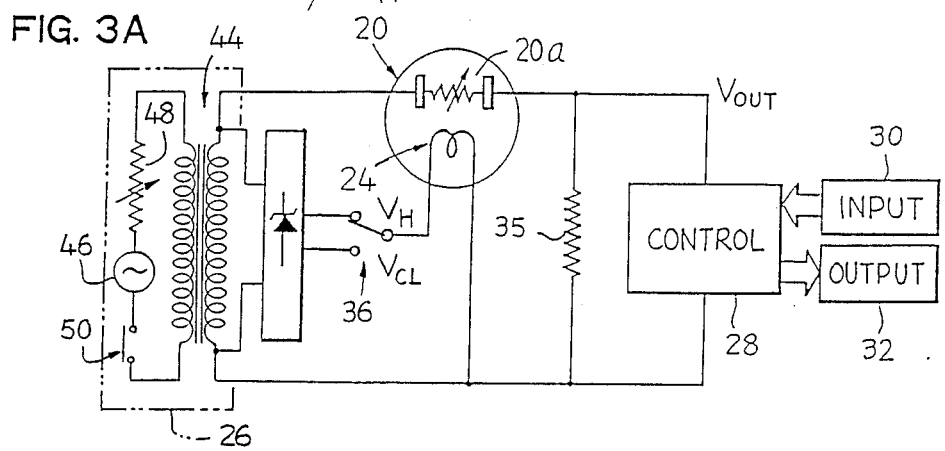
FIG. 3A is a diagram showing the circuit arrangement of a third preferred form of halitosis detector device basically arranged as shown in FIG. 1.
Figure 3B:
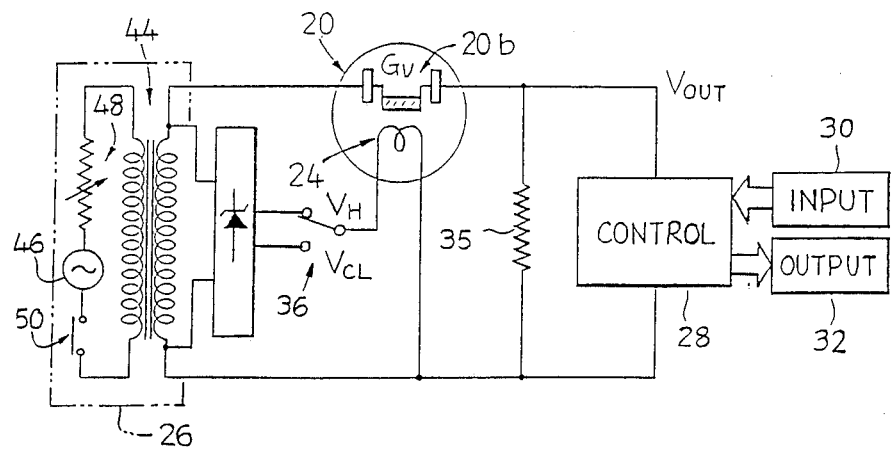
FIG. 3B is a diagram showing the circuit arrangement of a fourth preferred form of halitosis detector device basically arranged as shown in FIG. 1.

FIGS. 3A and 3B respectively show the circuit arrangements of third and fourth preferred forms of halitosis detector device basically constructed as described with reference to FIG. 1. The detector device shown in FIG. 3A is generally similar to the detector device described with reference to FIG. 2A and thus uses in the sensor unit 20 a thermally activated metal-oxide semiconductor sensor element 20a connected between the electrodes 22 and 22′. The constant-voltage power supply circuit 26 comprises a transformer 44 having a primary winding connected across a series combination of an a.c. power source 46, an adjustable voltage regulator 48 and a normally open power supply switch 50, and a secondary winding connected across the constant voltage generator circuit 34. The constant voltage generator circuit 34 may be of the type using a Zener diode by way of example and has terminals connected across the secondary winding of the transformer 44 and two taps connected across the switch circuit 36 to the heater element 24.

On the other hand, the halitosis detector device shown in FIG. 3B is generally similar to the detector device described with reference to FIG. 2B and uses in the sensor unit 20 a sensor element 20b implemented by a thermally activated thin-film adsorption-effect transistor provided between the electrodes 22 and 22′. As in the detector device of FIG. 2B, the constant-voltage power supply circuit 26 included in the embodiment herein shown comprises a transformer 44 having a primary winding connected across a series combination of an a.c. power source 46, an adjustable voltage regulator 48 and a normally-open power supply switch 50, and a secondary winding connected across the constant voltage generator circuit 34. The constant voltage generator circuit 34 may be of the type using a Zener diode by way of example and has terminals connected across the secondary winding of the transformer 44 and two taps connected across the switch circuit 36 to the heater element 24.

Figure 4:
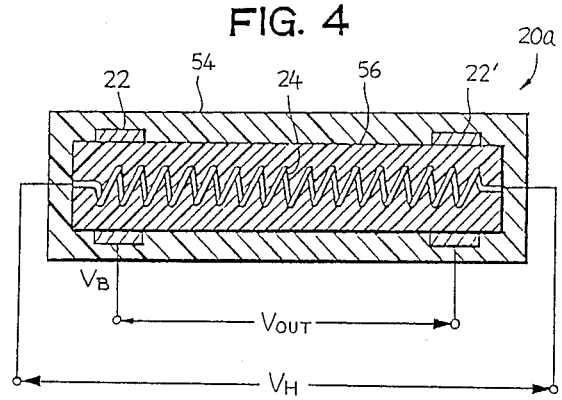
FIG. 4 is a longitudinal sectional view showing the detailed construction of a typical example of a thermally activated metal-oxide semiconductor sensor element used in the halitosis detector device shown in FIG. 2A or 3A.

In FIG. 4 of the drawings is shown the construction of a typical example of the thermally activated metal-oxide semiconductor sensor element 20a used in the halitosis detector device shown in FIG. 2A or 3A. The metal-oxide semiconductor sensor element 20a comprises a hollow cylindrical body of sintered tin dioxide 54 ($SnO_2$) and a body of electrical insulator 56 typically composed of sintered almina ceramics and enclosed in the body of tin dioxide 50. The body of tin dioxide 54 may have its outer peripheral surface covered with a protective coating of, for example, silicon dioxide ($SiO_2$), though not shown. The electrodes 22 and 22′ are embedded in the body of tin dioxide 54 and are located in the vicinity of the opposite ends, respectively, of the body of insulator 56, each of the electrodes 22 and 22′ being provided in the form of a ring. The heater element 24 is implemented by a coiled resistive wire and is embedded in the body of insulator 56 to longitudinally extend between the opposite ends of the body of insulator 56 each for connection to an external lead.

As described with respect to FIG. 1, a predetermined bias voltage $V_B$ is constantly applied between the electrodes 22 and 22′ so that a signal voltage $V_{OUT}$ higher than the fixed bias voltage $V_B$ and variable with the concentration of the detected reducing gases is produced between the electrodes 22 and 22′. To the hh 24 is selectively applied the heater voltage $V_H$ or the sensor cleaning voltage $V_H$ for heating the body of insulator 56 uniformly throughout the length of the body of insulator 56 between the electrodes 22 and 22′.

A metal-oxide semiconductor gas sensor of tin dioxide is per se well known in the art such as from the article "Inflammable- and Hazardous-Gas Detectors on the Way to Meeting Required Performance Characteristics", R. Okabe, ("The Sensors", pages 331–334, Nikkei McGrawhill, 1981). When the heater element 24 in the sensor unit 20 using the sensor element 20a shown in FIG. 4 is placed in an ambient containing reducing gases of prescribed compositions and is activated to heat the body of tin dioxide 54 to a certain temperature, the resistance $R_v$ through the body of tin dioxide 54 varies depending on the types of the reducing gases and with the concentration of the gases in the ambient. When the ambient to which the body of tin dioxide 54 is thus exposed contains a particular kind of inflammable reducing gas, the resistance $R_v$ through the body of tin dioxide 54 continuously varies with the concentration of the reducing gas with a characteristic specific to the chemical composition of the gas. The input/output characteristics of the sensor element 20a thus implemented by the tin dioxide metal-oxide semiconductor vary with the temperature to which the channel layer 64 is heated and may therefore be adjusted through selection of the heater voltage $V_H$ to be applied to the heater element 24.

It may be herein noted that, where the metal-oxide semiconductor sensor element 20a constructed as hereinbefore described is used as in each of the detector devices of FIGS. 2A and 3A, the heater voltage $V_H$ to be applied to the heater element 24 is selected such that the body of tin dioxide 54 in the sensor element 20a is heated to a temperature within the range of 250° C. to 400° C., or preferably approximating 280° C.

Figure 5:
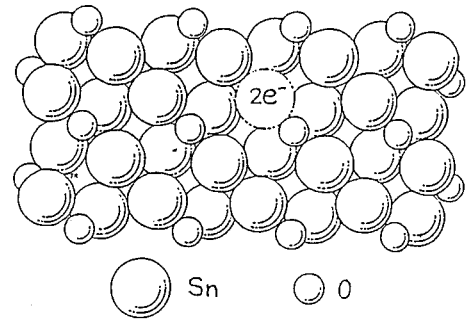
FIG. 5 is a diagram showing a portion of a crystalline lattice structure of tin dioxide forming part of the sensor element shown in FIG. 4.

FIG. 5 shows a portion of a crystalline lattice structure of tin dioxide, wherein the larger particles represent oxygen atoms and the smaller ones represent tin atoms. The crystal structure of tin dioxide normally stays in an oxygen-poor state and has lattice vacancies devoid of oxygen atoms, as indicated by dotted line. Electrons $2e^-$ are thus trapped at the oxygen vacant lattice sites of the crystal structure and thus form a relatively shallow energy level providing a donor level. When the crystal structure is heated to a temperature approximating 280° C., these electrons are activated toward the conduction band and produce charge carriers which contribute to electrical conduction, enabling the crystal structure to behave as an n-type semiconductor. When the crystal structure is placed in the ambient of air, ionized oxygen particles are caused to adhere to the surface of the structure so that potential barriers to electrons are established at the grain boundaries of the structure. The potential barriers thus established in the crystal structure form a resistance to the migration of charge carriers through the crystal structure. If, in this instance, the ambient of air to which the crystal structure has been exposed contains any kind of reducing gas, the molecules of the reducing gas are adsorbed to and combusted at the surface of the crystal structure with the agency of tin dioxide as the catalyst. This gives rise to reduction in the density of negative charges at the surface of the crystal structure with the result that the oxygen atoms at the grain boundaries in the structure are caused to move toward the surface of the structure. The movement of the oxygen atoms toward the surface of the structure in turn results in reduction in the potential barriers between the grain boundaries with a consequent decrease in the resistance to the migration of charge carriers through the crystal structure and accordingly in the resistance value of the structure as a whole. Thus, the resistance value of the crystal structure as a whole varies with the concentration of the reducing gas in the ambient to which the structure is exposed.

Heating the crystal structure to a temperature higher than the temperature used for the detection of the reducing gas gives rise to an increase in the density of negative charges at the surface of the crystal structure and accordingly in the potential barriers between the grain boundaries of the structure. This results in restoration of the initial resistance $R_v$ of the crystal structure and, thus, the contaminated sensor element 20a using the crystal structure of tin dioxide is regenerated or "cleaned".

It has been experimentally found by the inventor that the temperature to which the crystal structure of tin dioxide is to be heated is preferably about 1.5 times higher than the temperature used for the detection of malodorant gases. Thus, the sensor cleaning voltage $V_{CL}$ to be applied to the heater element 24 for cleaning the contaminated sensor element 20a is selected preferably such that the body of tin dioxide 56 of the sensor element 20a is heated to a temperature which is about 1.5 times higher than the temperature used for the detection of malodorant gases. Where the heater voltage $V_H$ to be used for the detection of malodorant gases is selected so that the body of tin dioxide 56 is heated to about 280° C. as previously noted, the sensor cleaning voltage $V_{CL}$ may thus be selected such that the body of tin dioxide 56 is heated to about 420° C.

FIG. 6 shows the construction of a typical example of the thermally activated thin-film adsorption-effect transistor implementing the AET sensor element 20b used in the detector device shown in FIG. 2B or 3B.

As shown, the AET sensor element 20b comprises a substrate 58 of, typically, ceramic having a heater element 24 attached to one or lower surface thereof and a pair of electrodes 22 and 22' attached to the other or upper surface thereof. The electrodes 22 and 22' are located in the vicinity of the opposite ends, respectively, of the ceramic substrate 58. The heater element 24 extends longitudinally between the opposite ends of the ceramic substrate 58 so that the substrate 58 can be heated throughout its area. On the upper surface of the ceramic substrate 58 is deposited or otherwise formed first and second doped semiconductor layers respectively implementing drain and source regions 60 and 62 of the adsorption-effect transistor. These drain and source regions 60 and 62 are deposited in part on the upper surface of the substrate 58 and in part on the electrodes 22 and 22', respectively. Thus, the drain and source regions 60 and 62 have respective portions 60a and 62a which directly overlie the surface of the substrate 58 and which are spaced apart from each other to allow the surface of the substrate 58 to be exposed between the regions 60 and 62. Each of the drain and source regions 60 and 62 is fabricated from typically a layer of silicon doped with arsenic by the known ion implantation techniques. On this exposed area of the upper surface of the ceramic substrate 58 between the portions 60a and 62a of the drain and source regions 60 and 62 is formed a gate electrode 64 which is attached directly to the surface of the substrate 58 and which underlies a semiconductor insulator layer 66 of, typically, silicon dioxide ($SiO_2$).

The adsorption-effect transistor implementing the sensor element 20b further comprises a channel layer 68 of, typically, silicon doped with indium dioxide ($InO_2$), zinc dioxide ($NnO_2$) or tin dioxide $SnO_2$). The channel layer 68 extends in part into the drain region 60 and in part into the source region 62 and has on the insulator layer 66 a surface area exposed between the drain and source regions 60 and 62. The adsorption-effect transistor thus configured acts similarly to an n-channel metal-oxide-semiconductor (MOS) field-effect transistor (FET) and has a channel region subjected to an ambient through the exposed area of the channel layer 68.

A predetermined drain voltage is applied as the previously mentioned bias voltage $V_B$ to the electrode 22 contacting the drain region 60 so that a signal voltage $V_{OUT}$ higher than the fixed bias voltage $V_B$ and variable with the concentration of the detected reducing gases is produced between the electrodes 22 and 22'. To the heater element 24 is applied the heater voltage $V_H$ for heating the channel layer 68 through the ceramic substrate 58 throughout the length of the channel layer 68 between the drain and source regions 60 and 62.

When the channel layer 68 of the sensor element 20b thus configured is heated with the heater element 24 electrically activated by the heater voltage $V_H$, the atoms of the reducing gases contained in the ambient to which the channel layer 68 is subjected over its exposed surface area are adsorbed to the channel layer 68 and are ionized therein. The electric field thus induced as a result of the ionization of the atoms thus adsorbed to the channel layer 68 causes variation in the conductivity $G_y$ through the channel region between the drain and source regions 60 and 62 depending on the chemical composition of the ambient. When the ambient contacting the exposed surface area of the channel layer 68 contains a particular kind of inflammable reducing gas, the conductance $G_y$ through the channel layer 68 continuously varies with the concentration of the reducing gas with a characteristic specific to the chemical composition of the particular gas. The input/output characteristics of the sensor element 20b thus implemented by the adsorption-effect transistor vary not only with the temperature to which the channel layer 68 is heated but also with the gate voltage $V_G$ applied to the gate electrode 64. The input/output characteristics of the sensor element 20b may therefore be adjusted through selection of not only the heater voltage $V_H$ to be applied to the hh 24 but also the gate volta $V_G$ to be applied to the gate electrode 64.

FIGS. 7A, 7B and 7C show the external and internal constructions of a preferred embodiment of a halitosis detector device incorporating the arrangement described with reference to FIG. 2A.

The detector device herein shown comprises a casing 70 which has internal partition walls 72, 74 and 76 defining four separate chambers which consist of a control compartment 78, a sensor chamber 80, a battery cell compartment 82 and a switch compartment 84. In the control compartment 78 are provided a control unit 86 incorporating the control circuit 28 and input and output networks 30 and 32 of the detector device described with reference to FIG. 2A or 2B, and a voltage regulator unit 88 implemented by the variable resistor 40 included in the device shown in FIG. 2A or 2B. In association with the voltage regulator unit 88 is provided a manually-operated voltage adjustment wheel 90 to be used for continuously varying the voltage across the variable resistor 40 and accordingly each of the bias, heater and sensor cleaning voltages $V_B$, $V_H$ and $V_{CL}$ to be used in the detector device.

In the control compartment 78 of the casing 70 may be further provided an air discharge fan 92 driven by a fan-drive motor 94 under the control of the control unit 86. The air discharge fan 92 has an air outlet communicating with the sensor chamber 80 through an opening 96 formed in the partition wall 74. In the sensor chamber 80 is located the sensor unit 20 which is assumed by way of example to be implemented by the metal-oxide semiconductor sensor element 20a described with reference to FIG. 4. If desired, however, the sensor unit 20 of the device herein shown may be provided in the form of the adsorption-effect transistor sensor element 20b described with reference to FIG. 6. The sensor chamber 80 is open to the atmosphere through a blow-in opening 98 formed in the upper panel portion of the casing 70 and preferably provided with a suitable filter element as shown. The blow-in opening 98 provides means through which the air exhaled by a subject to be examined for halitosis is to be blown into the sensor chamber 80. The air discharge fan 92 is used for scavenging the sensor chamber 80 so that the air which has thus been blown into the sensor chamber 80 through the blow-in opening 98 is to be purged out of the chamber 80 upon termination of each cycle of testing operation. In the casing 70 may thus be further formed vent holes 100 through which air is to be forced out of the sensor chamber 80 when the fan 92 is in operation.

The power supply chamber 80 is provided for the accommodation of battery cells 102 implementing the d.c. power source 38 which forms part of the power supply circuit 26 in the detector device of FIG. 2A. The battery cells 102 are shown arranged in series between a contact plate 104 and a conductive coil spring 106 and are electrically connected to the control unit 86, voltage regulator unit 88 and fan-drive motor 94 through suitable leads and wires (not shown) and across a manually-operated power supply switch assembly 108. The power supply switch assembly 108 is provided in the switch compartment 84 and implements the normally-open power supply switch 42 in the detector device of FIG. 2A.

The detector device thus constructed further comprises a plurality of indicators which are arranged to be visible through apertures formed in the upper panel portion of the casing 70. These indicators are implemented by light emitting diodes (LEDs) which form part of the output network 32 included in the control unit 86. As will be described in more detail, the indicators include a first indicator 110a to be turned on to illuminate or flicker when the device is switched in, and a second indicator 110b to be turned on to illuminate or flicker when it is confirmed that the bias voltage $V_B$ of a predetermined level is established. The indicators provided in the device shown in FIGS. 7A to 7C further include third to fifth indicators 110c to 110e which are to be turned on to illuminate or flicker respectively when predetermined degrees of malodorousness of exhalation are detected.

Figure 8:
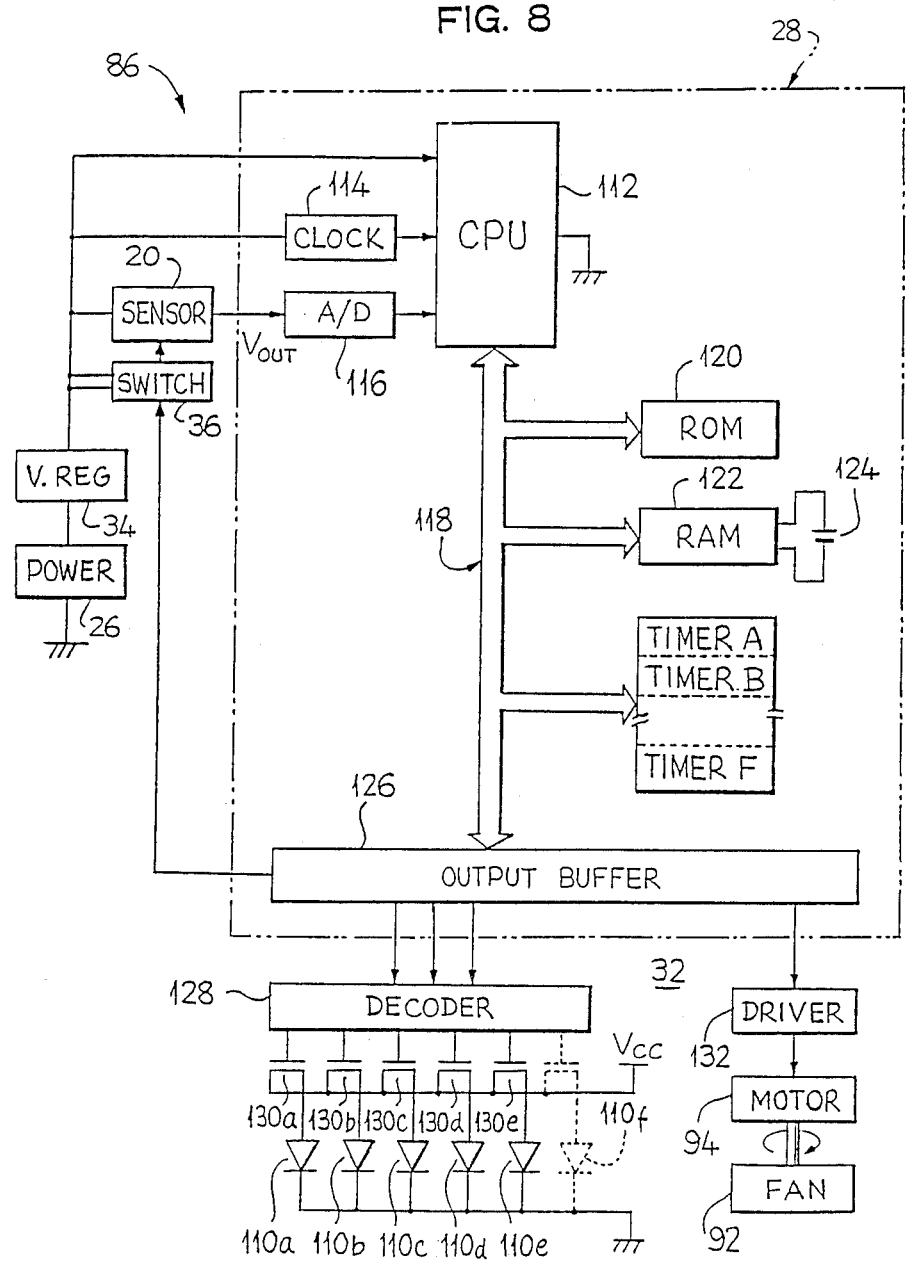
FIG. 8 is a diagram showing a preferred example of the arrangement of the control circuit and output network which form part of the control unit incorporated in the halitosis detector device illustrated in FIGS. 7A to 7C.

FIG. 8 shows a preferred example of the circuit arrangement of the control circuit 28 and output network 32 which form part of the control unit 86 incorporated in the device hereinbefore described with reference to FIGS. 7A to 7C.

The control circuit 28 forming part of the control unit 86 comprises a single-chip central processing unit 112 electrically connected to the power supply circuit 26 and responsive to clock pulses supplied from a clock pulse generator 114 which is also connected to the power supply circuit 26. The signal voltage $V_{OUT}$ produced by the sensor unit 20 is supplied to an analog-to-digital converter 116 and is input in the form of a digital signal to the central processing unit 112. The central processing unit 112 in turn is connected through a common bus 118 to a read-only memory (ROM) unit 120, a random access memory (RAM) unit 122, and a set of timers "A", "B", "C", . . . as shown. The read-only memory unit 120 has stored therein instructions and data in accordance with which the central processing unit 112 is to operate to execute the main routine program. In the random-access memory unit 122 are stored the data and instructions which may be entered by the operator and the data and instructions which may be fetched by the central processing unit 112 from the memory 120. The random-access memory unit 122 is provided with a backup power source 124 which refreshes the contents of the memory unit 122. While the memory units 120 and 122 are thus assumed to be provided externally of the single-chip central processing unit 112, such units may be implemented by the internal read-only and random-access memories, respectively, of the central processing unit 112. The timers "A", "B", "C", . . . operate on the clock pulses supplied from the clock pulse generator 114 and are set for periods of time to dictate the time intervals for which various subroutines are to be executed under the control of the central processing unit 112. The timers "A", "B", "C", . . . may also be implemented by the internal timers which may be provided in the central processing unit 112. The common bus 118 leading from the central processing unit 112 terminates in an output buffer 126 through which various control signals to be supplied to the fan-drive motor 94 and indicators 110a to 110e are output from the output network 32.

In the circuit arrangement herein shown, the output network 32 comprises a decoder circuit 128 having input terminals connected to the buffer 126 and parallel output terminals respectively connected through switch elements 130a to 130e to the light emitting diodes implementing the indicators 110a to 110e. Each of the switch elements 130a to 130e is implemented by a field-effect transistor which has its gate connected to the decoder circuit 128 and its source-drain current path connected between a supply voltage source $V_{CC}$ and the anode terminal of the associated one of the diodes implementing the indicators 110a to 110e. The output network 32 in the circuit arrangement shown in FIG. 8 further comprises a driver circuit 132 for the fan-drive motor 94 for driving the air discharge fan 92. The output buffer 126 is further connected to the switch circuit 36 so that either the heater voltage $V_H$ or the sensor cleaning voltage $V_{CL}$ is selectively supplied to the heater element 24 under the control of the central processing unit 112, as will be described in more detail.

Figure 9B:
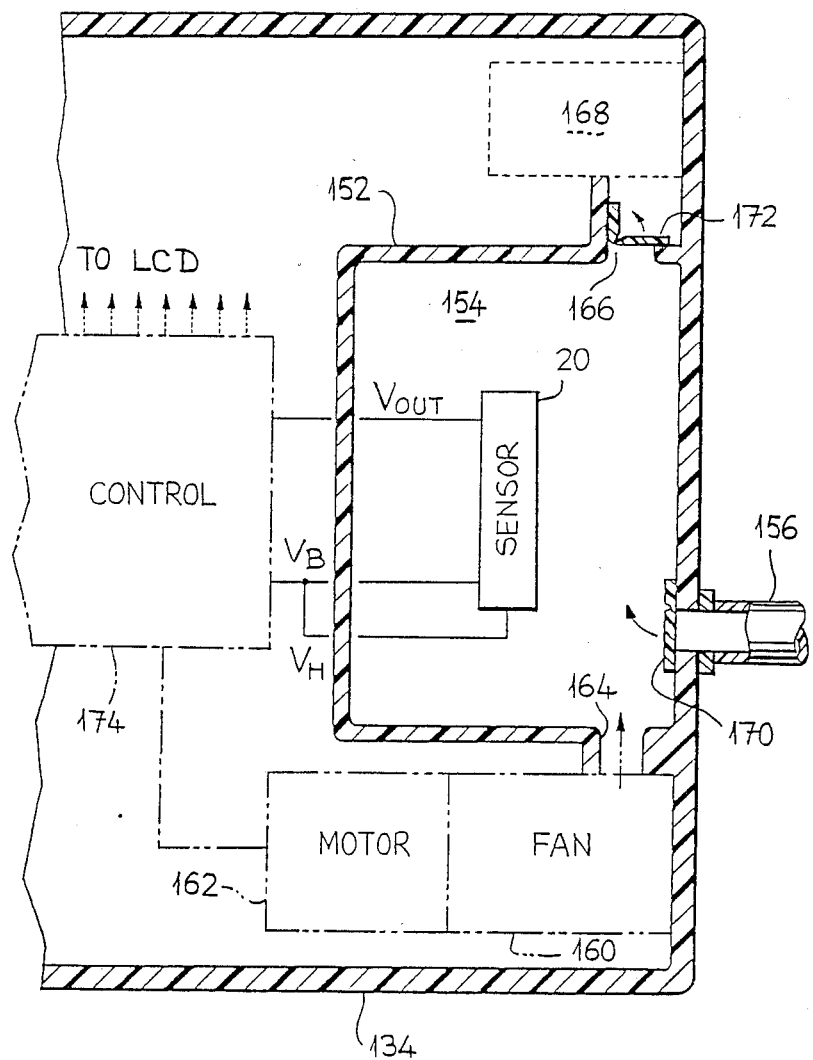
FIG. 9B shows part of the internal construction of the halitosis detector device having the external construction illustrated in FIG. 9A.

FIG. 9A shows the external construction and FIG. 9B shows part of the internal construction of a preferred embodiment of a halitosis detector device incorporating the arrangement described with reference to FIG. 3A.

Referring first to FIG. 9A, the detector device comprises a casing 134 having a control panel 136 and a display screen 138. The display screen 138 comprises three sections which consist of a graphic display section 138a, a numerical data display section 138b and a message display section 138c. The graphic display section 138a is used to display the result of the test in the form of, for example, a bar graph. The data display section 138b is used to display the result of the test in the form of a numerical value. The message display section 138c is used to display messages and instructions to be given to the operator at various stages of testing operation. Each of the sections 138a, 138b and 138c of the display screen 138 is implemented typically by a liquid crystal display panel.

On the other hand, the control panel 136 comprises various manually operated control keys which include a test start key 140, a test end key 142, a prompt key 144, a clockmode select key 146, and a print request key 148.

The test start key 140 is to be used to start a cycle of testing operation with the power supply switch 42 depressed preliminary. The test end key 142 is to be used to put an end to the cycle of testing during or upon termination of the testing operation. The prompt key 144 is used to clear the message currently appearing on the graphic display section 138a of the display screen 138 and prompt the device to display another message, if any, on the display section 138a. The clock-mode select key 146 is used to request the device to operate as a clock numerically indicating the month, day, hour and minute on the data display section 138b of the display screen 138 when the device is out of use for testing purposes. The print request key 148 is provided in association with a printer (not shown) which may form part of the device embodying the present invention and is used to request the printer to print the result of the test on display. On the control panel 136 is further provided a manually-operated voltage regulator adjustment wheel 150 arranged in association with the voltage regulator unit 88 (FIG. 3A or 3B) for continuously varying the voltage across the variable resistor 40 and accordingly each of the bias, heater and sensor cleaning voltages $V_B$, $V_H$ and $V_{CL}$ to be used in the detector device.

Turning to FIG. 9B, the casing 134 of the detector device comprises an internal partition wall 152 defining a sensor chamber 154 in which is located the sensor unit 20. The sensor unit 20 is also assumed by way of example to be implemented by the metal-oxide semiconductor sensor element 20a described with reference to FIG. 4 but, if desired, may be provided in the form of the adsorption-effect transistor sensor element 20b described with reference to FIG. 6. The sensor chamber 154 is open to the atmosphere through a flexible blow-in tube 156 terminating in a mouthpiece 158 shown in FIG. 9A. The blow-in tube 156 and mouthpiece 158 provide means through which the air exhaled by a subject to be examined for halitosis is to be blown into the chamber 154.

In the casing 154 of the device is preferably further provided an air discharge fan 160 located adjacent the sensor chamber 154 and driven by a fan-drive motor 162. The air discharge fan 160 has an air outlet communicating with the sensor chamber 154 through an opening 164 formed in the partition wall 152. The fan 160 is used for scavenging the sensor chamber 154 so that the air which has been blown into the sensor chamber 154 through the blow-in tube 156 is purged out of the chamber 154 upon termination of each cycle of testing operation. In the partition wall 152 of the casing 134 is thus further formed an air outlet opening 166 which communicates with a vent hole 168 formed in the upper panel portion of the casing 134 and open to the atmosphere as will better seen from FIG. 9A. The fan-drive motor 162 may be of the reversible type so that the air discharge fan 160 operates as a suction fan. When a subject breathes with the mouthpiece 158 put into his mouth during testing, the flow of the air breathed into the tube 156 is forcibly inducted into the sensor chamber 154 by the air discharge fan 160 driven to operate as a suction fan to assist the subject in blowing into the tube 156.

At the air outlet end of the blow-in tube 156 into the sensor chamber 154 is located a check valve 170 adapted to open the outlet end of the tube 156 in response to a forced flow of air blown into the blow-in tube 156. The check valve 170 closes the outlet end of the tube 156 when the pressure of air in the sensor chamber 154 is higher than the air pressure in the tube 156. In the air outlet opening 166 is also provided a check valve 172 which is adapted to remain closed in the presence in the chamber 154 of an air pressure resulting from the air exhaled by a subject and blown into the chamber 154. The check valve 172 is thus caused to open when the pressure of air in the sensor chamber 154 becomes higher than a predetermined level higher than the pressure developed by the air exhaled and blown into the chamber 154.

Within the casing 134 of the device is further accommodated a control unit 174 incorporating the control circuit 28 and input and output networks 30 and 32 of the detector device described with reference to FIG. 3A. The control unit 174 is electrically connected to the sensor unit 20 and fan-drive motor 162 and further to the liquid crystal display panels forming the display sections 138a, 138b and 138c through the power supply switch 42.

Figure 10:
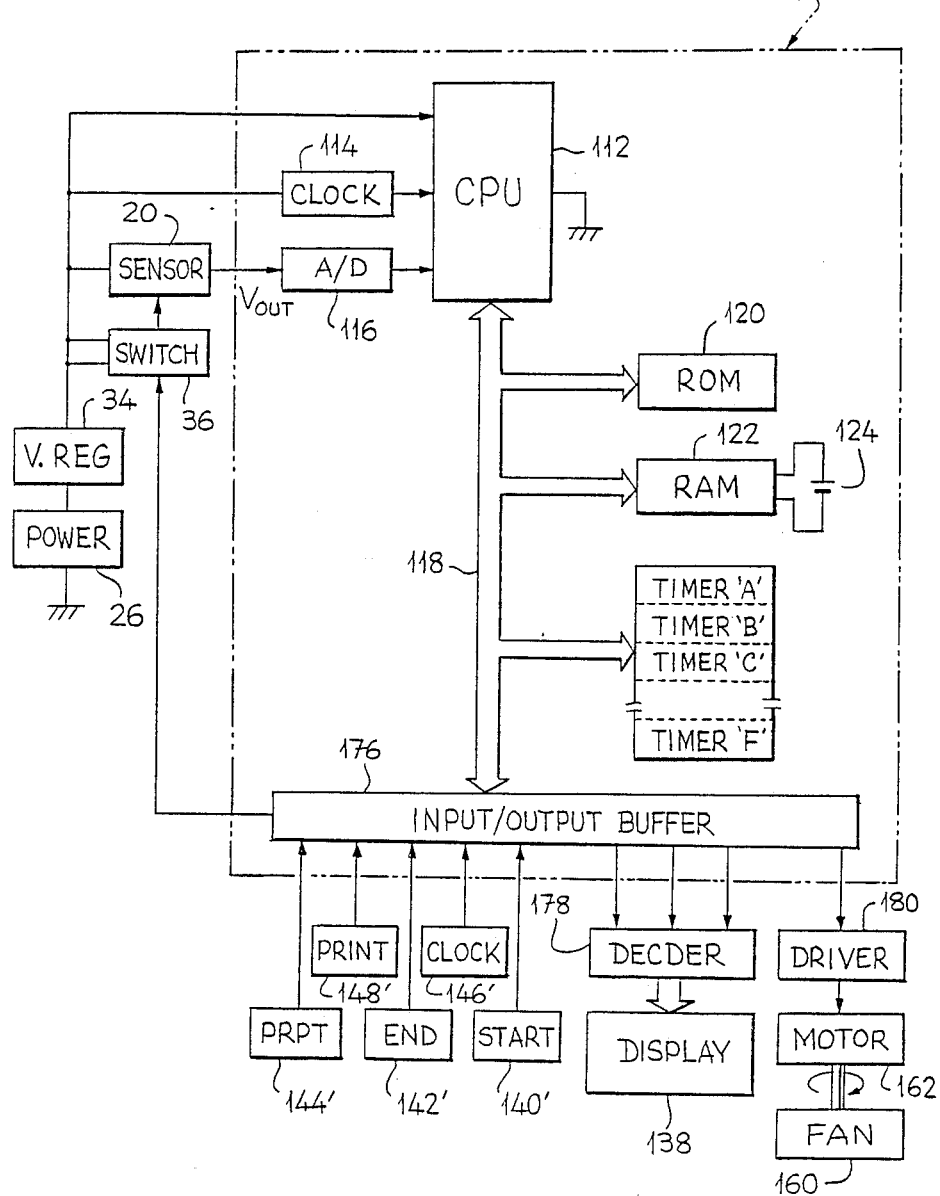
FIG. 10 is a diagram similar to FIG. 8 but now shows a preferred example of the arrangement of the control circuit and input and output networks incorporated in the halitosis detector device illustrated in FIGS. 9A and 9B.

FIG. 10 shows a preferred example of the circuit arrangement of the control circuit 28 and input and output networks 30 and 32 which may be incorporated in the detector device hereinbefore described with reference to FIGS. 9A and 9B.

The control circuit 28 forming part of the control unit 174 shown in FIG. 9B is per se similar to the control circuit 28 described with reference to FIG. 8 and, thus, comprises a single-chip central processing unit 112 (CPU), a clock pulse generator 114, and an analog-to-digital converter 116. The central processing unit 112 is connected via a bidirectional common bus 118 to a read-only memory unit 120, a random-access memory unit 122, and a set of timers "A", "B", "C", ... which are all similar to their respective counterparts in the circuit arrangement described with reference to FIG. 8. The common bus 118 leading from the central processing unit 112 terminates in an input/output buffer 176 through which various signals to be supplied to the central processing unit 112 are input from the input network 30 and control signals to be supplied to the display screen 138, fan-drive motor 162 and printer (not shown) are output to the output network 32.

In the circuit arrangement herein shown, the input network 30 comprises switches 140', 142', 144', 146' and 148' associated with the test start key 140, test end key 142, prompt key 144, clock-mode select key 146, and print request key 148, respectively, on the control panel 136. Each of these switches 140' to 148' is operated to close with the associated one of the keys 140 to 148 manually depressed and supplies a corresponding control to the central processing unit 112 through the input-/output buffer 176. On the other hand, the output network 32 in the circuit arrangement shown in FIG. 10 comprises a decoder circuit 178 having input terminals connected to the buffer 176 and output terminals connected to the liquid crystal display panels forming the sections 138a to 138c of the display screen 138. As in the circuit arrangement described with reference o FIG. 8, the output network 32 further comprises a driver circuit 180 for the fan-drive motor 162 for driving the air discharge fan 160 and the input/output buffer 176 is further connected to the switch circuit 36. Either the heater voltage $V_H$ or the sensor cleaning voltage $V_{CL}$ is thus selectively supplied to the heater element 24 under the control of the central processing unit 112.

In the meantime, it has been experimentally confirmed that the minimum concentrations (in parts per million) of the reducing gases forming typical malodorants in human exhalations perceivable to be foul are as follows:

Ethyl mercaptan, $C_2H_5SH$: 0.0010 ppm
Methyl mercaptan, $CH_3SH$: 0.0021 ppm
Hydrogen sulfide, $H_2S$: 0.0047 ppm
Dimethylamine, $(CH_3)_2NH$: 0.0470 ppm
Acrylonitrile, $CH_2=CHCN$: 21.4000 ppm
Methanol, $C_2H_5OH$: 100.0000 ppm Dimethylamine and acrylonitrile are the major sources of the malodor caused by the eating of fish and garlic, respectively, while methanol is typical of the smells of alcoholic breaths. Methyl mercaptan is typical of the malodorants contained in morbidly malodorous human exhalations. The results of the quantitative analysis conducted using gas chromatography show that the concentration of methyl mercaptan is less than 2.0 ppm and ordinarily ranges from about 0.2 ppm to about 0.7 ppm in the exhalations of patients who are suffering from morbid halitosis. The concentration of this range equals approximately 100 to 350 times the minimum concentration (0.0021 ppm) of methyl mercaptan in human exhalations perceivable to be malodorous. This suggests that the bias and heater voltages $V_B$ and $V_H$ to be used in a detector device according to the present invention may be selected so that the sensor unit 20 of the device is capable of detecting malodorants of concentrations slightly higher than a value corresponding to 2.0 ppm of methyl mercaptan. When the output voltage $V_{OUT}$ from the sensor unit 20 indicates that the detected total concentration of malodorants is higher than such a value, it is presumed and is quite likely that the data represented by the voltage $V_{OUT}$ has resulted simply from the eating of fish and/or garlic and/or the drinking of an alcoholic beverage. In this instance, it may be determined that the subject under examination is in a physical condition not qualified for testing and, as such, the result of the test may be regarded as being invalid or meaningless for purposes of diagnosis. The test for such a subject may thus be redone when it is confirmed that the subject is in a physical condition properly qualified for testing.

FIGS. 11A to 11D are flowcharts respectively showing preferred examples of the main routine program which may be executed by the central processing unit 112 incorporated in the control circuit 28 described with reference to FIG. 8 or the control circuit 28 described with reference to FIG. 10. In the routine program shown in FIG. 11A is assumed that the device described with reference to FIGS. 7A to 7C is devoid of the air discharge fan 92 or the device described with reference to FIGS. 9A and 9B is devoid of the air discharge fan 160. The main routine program shown in FIG. 11C is adapted for use particularly in the device described with reference to FIGS. 9A and 9B.

The main routine program shown in FIG. 11A starts with the power supply switch 42 closed manually and first proceeds to subroutine A01 to initialize the central processing unit 112. The central processing unit 112 then executes a sensor cleaning subroutine A02 to energize the heater element 24 of the sensor unit 20 with the sensor cleaning voltage $V_{CL}$ for cleaning the sensor element 20a which may have been left contaminated after the latest use of the detector device. Upon termination of the sensor cleaning subroutine A02, the central processing unit 112 executes a level adjustment subroutine A03 to confirm whether or not the bias voltage $V_B$ to be applied to the sensor element 20a is of a correct level. If it is found that the bias voltage $V_B$ to be applied to the sensor element 20a is of an improper level, the central processing unit 112 waits until the voltage $V_B$ is adjusted to the correct level by means of the voltage regulator 48. The adjustment of the voltage from the voltage regulator 48 is made by manipulation of the voltage adjustment wheel 90 of the device shown in FIGS. 7A to 7C or the voltage adjustment wheel 150 of the device shown in FIGS. 9A and 9B. Each of the bias, heater and sensor cleaning voltages $V_B$, $V_H$ and $V_{CL}$ to be used in the detector device is thus adjusted to a correct value by manipulation of the voltage adjustment wheel 90 or 150.

At a desired point of time after the device has been switched in, the subject to be tested for halitosis may blow into the device through the blow-in opening 98 in the device shown in FIGS. 7A to 7C or the blow-in tube 156 of the device shown in FIGS. 9A and 9B. Thus, the central processing unit 112 executes a test/display subroutine A04 to perform the testing operation and display the result of the test by any of the indicators 110c to 110e of the device shown in FIGS. 7A to 7C or on the display window 138 of the device shown in FIGS. 9A and 9B. The details of this routine program as applied to the device shown in FIGS. 7A to 7C will be described with reference to FIGS. 12A and 12B. Where the routine program shown in FIG. 11A is to be executed in the device of FIGS. 7A to 7C, the result of the test is compared with predetermined reference values so that any one of the indicators 110c to 110e is selectively turned on to illuminate or flicker depending on the degree of seriousness of the halitosis detected. The main routine program shown in FIG. 11A may be modified so that the sensor cleaning subroutine A02 is to be executed subsequently to the test/display subroutine A04.

The main routine program shown in FIG. 11B features an additional subroutine A05 by which the air discharge fan 92 in the device shown in FIGS. 7A to 7C or the air discharge fan 160 in the device shown in FIGS. 9A and 9B is actuated to scavenge the sensor chamber 80 in the former device or the sensor chamber 154 in the latter device. The details of the forced air discharge subroutine A05 to be executed additionally to the routine program of FIGS. 12A and 12B will be described with reference to FIG. 13. The main routine program shown in FIG. 11B may be modified so that the sensor cleaning subroutine A02 is to be executed subsequently to the test/display subroutine A04 or to the air discharge subroutine A05.

In the main routine program shown in FIG. 11C are performed two or more cycles of testing operation repeatedly for a single subject by the test/display subroutine A04 subsequently to the level adjustment subroutine A03. During each cycle of testing operation, the air discharge or scavenge subroutine A05 is executed subsequently to the test/display subroutine A04. After execution of the air discharge or scavenge subroutine A05 in the final cycle of testing operation, the arithmetic mean of the values indicating the results of the tests conducted is calculated and displayed by a mean calculation subroutine A06 and may be output in the form of printed information by subroutine print output A07. The details of the routine program including these subroutines A04, A05, A06 and A07 as applied to the device of FIGS. 9A and 9B will be described with reference to FIGS. 14A to 14D.

The mean value of the results of the tests as calculated in the test/display subroutine A04 may be compared with predetermined reference values as in a diagnosis subroutine A08 included in the main routine program illustrated in FIG. 11D. This diagnosis subroutine A08 is alternative to the mean calculation subroutine A06 in the routine program of FIGS. 14A to 14D. The details of such a diagnosis subroutine A08 will be described with reference to FIG. 15.

Figure 12A:
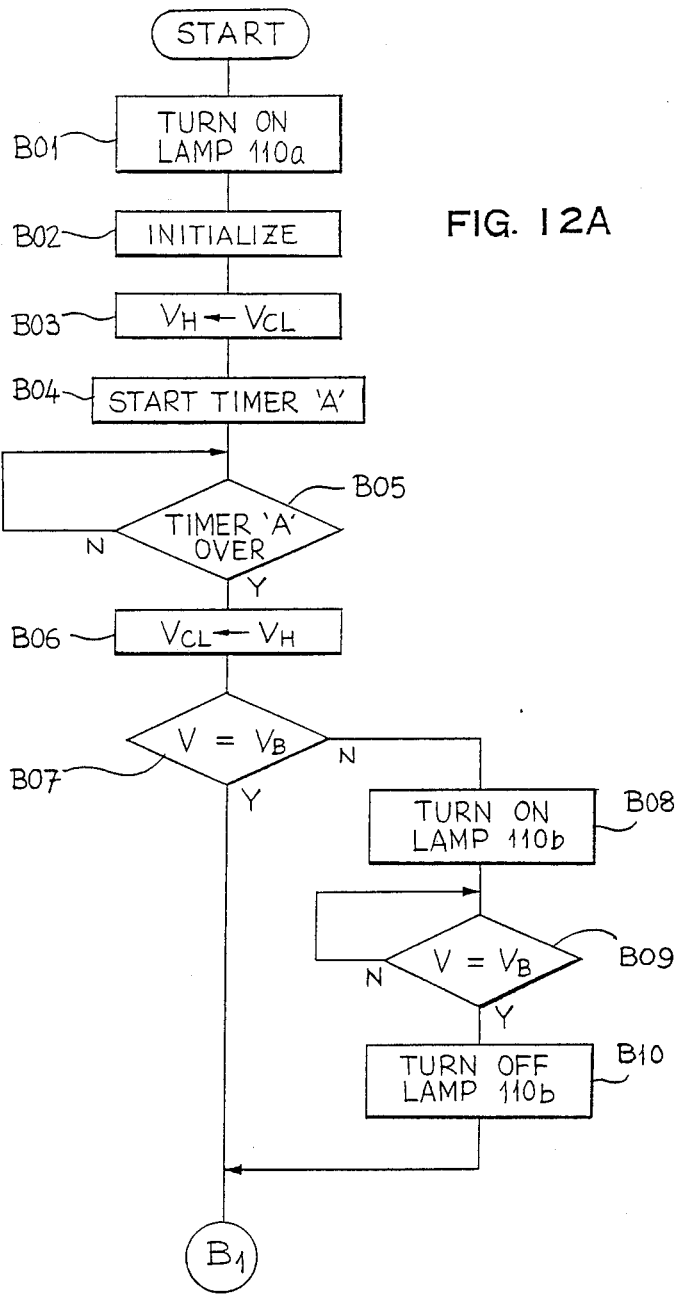

The routine program illustrated in FIGS. 12A and 12B is applied to the device shown in FIGS. 7A to 7C and is to be executed by the central processing unit 112 included in the control circuit 28 shown in FIG. 8. The routine program starts with the power supply switch 42 closed manually and first proceeds to step B01 for turning on the first indicator 110a of the device shown in FIGS. 7A to 7C to indicate that the device is switched in. After the first indicator 110a is thus turned on to illuminate or flicker, the subject may blow into the device through the blow-in opening 98 so that the air exhaled by the subject is admitted into the sensor chamber 80.

Subsequently to the step B01, the routine program proceeds to step B02 to initialize the central processing unit 112 and RAM unit 122 of the control circuit 28 to set up various operational parameters and modes of operation in accordance with prescribed default rules. The step B02 is followed by step B03 at which a control signal is issued from the output buffer 126 to the switch circuit 36 to select the sensor cleaning voltage $V_{CL}$ as an input to the heater element 24. The sensor cleaning voltage $V_{CL}$ being thus applied to the heater element 24, the sensor element 20a is heated to a temperature of typically 420° C. and is cleared of the contaminants which may have been left thereon after the latest use of the detector device. Upon termination of the sensor cleaning step B03, an instruction signal is issued from the central processing unit 112 as at step B04 to start the timer "A" incorporated in the control circuit 28. The timer "A" is set for a period of time predetermined for the cleaning of the sensor element 20a. When it is confirmed at a decision step B05 that the time set by the timer "A" has lapsed, a control signal is issued from the output buffer 126 to the switch circuit 36 to shift the input voltage for the heater element 24 from the sensor cleaning voltage $V_{CL}$ to the heater voltage $V_H$ as at step B06.

It is then confirmed at decision step B07 whether or not the voltage applied to the sensor element 20a is correctly of the predetermined bias level $V_B$. If it is found at this step B07 that the voltage applied to the sensor element 20a is higher or lower the level $V_B$, the central processing unit 112 issues an instruction signal at step B08 to turn on the second indicator 110b of the device to illuminate or flicker. The operator of the device is thus requested to adjust the sensor voltages through manipulation of the voltage adjustment wheel 90. The voltage adjustment wheel 90 will be then manipulated by the operator to continuously vary the voltage across the variable resistor 40 and accordingly each of the bias, heater and sensor cleaning voltages $V_B$, $V_H$ and $V_{CL}$ to be used in the detector device. When it is confirmed at step B09 that the voltage applied to the sensor element 20a has been correctly adjusted to the level $V_B$, an instruction signal is issued at step B10 to turn off the second indicator 110b.

The air exhaled by the subject having been admitted into the sensor chamber 80, the voltage $V_{OUT}$ produced across the sensor element 20a is increased to a level which is higher than the bias voltage $V_B$ and which varies with the concentration of the malodorants contained in the air in the chamber 80. Subsequently to the step B09 or when it is found at the step B07 that the voltage applied to the sensor element 20a is correctly of the level $V_B$, it is detected at a decision step B11 (FIG. 12B) whether or not the voltage $V_{OUT}$ currently present across the sensor element 20a is higher than the bias voltage $V_B$. In this instance, the voltage $V_{OUT}$ may be compared not with the bias voltage $V_B$ per se but preferably with a voltage slightly higher than the bias voltage $V_B$. This is because of the fact that the resistance and accordingly the voltage across the sensor element 20a will be caused to more or less vary when the element 20a is heated with the heater element 24 energized with the heater voltage $V_H$.

If the subject has blown into the device by the point of time when the step B11 is reached, the answer for the step B11 is given in the affirmative. In this instance, it is further queried at a decision step B12 whether or not the voltage $V_{OUT}$ currently produced across the sensor element 20a is lower than a predetermined first reference value $V_1$. This first reference value $V_1$ is higher than the bias voltage $V_B$ and is representative of the upper limit of the degrees of malodorousness of human exhalations determined to be normal and permissible. Such a limit of the permissible degrees of malodorousness may be selected to correspond to 0.2 ppm of methyl mercaptan for the reason explained hereinbefore. When it is determined at step B12 that the voltage $V_{OUT}$ currently produced across the sensor element 20a is lower than the first reference value $V_1$, an instruction signal is issued from the central processing unit 112 as at step B13 to turn on the third indicator 110c of the device to illuminate or flicker. The third indicator 110c will be turned on to illuminate or flicker if the subject has not blown into the device by the point of time the cleaning of the sensor element 20a is terminated at step B06.

If it is found at step B12 that the voltage $V_{OUT}$ across the sensor element 20a is not lower than the first reference value $V_1$, then it is tested at a decision step B14 whether or not the voltage $V_{OUT}$ is lower than a predetermined second reference value $V_2$. This second reference value $V_2$ is higher than the first reference value $V_1$ and is representative of the upper limit of the degrees of malodorousness of human exhalations determined to be serious and impermissible. Such a limit of the impermissible degrees of malodorousness represented by the second reference value $V_2$ of the voltage $V_{OUT}$ may be selected to correspond to 0.5 ppm of methyl mercaptan. When it is determined at step B14 that the voltage $V_{OUT}$ produced across the sensor element 20a is lower than such a second reference value $V_2$, an instruction signal is issued from the central processing unit 112 as at step B15 to turn on the fourth indicator 110d of the device to illuminate or flicker. If it is found at step B14 that the voltage $V_{OUT}$ produced across the sensor element 20a is not lower than the second reference value $V_2$, an instruction signal is issued from the central processing unit 112 as at step B16 to turn on the fifth indicator 110e of the device to illuminate or flicker. The illumination or flickering of the fifth indicator 110e is thus indicative of the fact that the subject's halitosis is of an abnormal degree and that the subject is diagnosed to be suffering from serious ozostomnia.

Subsequently to any of the steps B13, B15 and B16, the routine program proceeds to a step B17 at which an instruction signal is issued from the central processing unit 112 to start the timer "B" in the control circuit 28 shown in FIG. 8. The timer "B" is set for a period of time for which each of the indicators 110c to 110e to indicate the result of the test is to remain in the illuminating or flickering state. When it is thereafter confirmed at step B18 that the time set by the timer "B" has lapsed, an instruction signal is issued from the central processing unit 112 at step B19 to turn off the indicator 110c, 110d or 110e which has been turned on. After the indicator 110c, 110d or 110e is thus turned off at step B19, the routine program reverts to step B02 and may repeat the steps B02 to B19 as hereinbefore described.

Furthermore, the detector device shown in FIGS. 7A to 7B may be provided with a sixth indicator as indicated at 110f in FIG. 10 with slight modification made in the routine program hereinbefore described with reference to FIGS. 12A and 12B. In this instance, the routine program hereinbefore described may be modified so that, when it is found at step B12 that the voltage $V_{OUT}$ is not lower than the second reference value $V_2$, it is further tested whether or not the voltage $V_{OUT}$ is lower than a predetermined third reference value $V_3$ as at step 20 shown in FIG. 13. This third reference value $V_3$ is higher than the second reference value $V_2$ and is representative of the lower limit of the degrees of malodorousness of human exhalations to result from the eating of fish and/or garlic and/or the drinking of an alcoholic beverage. Such a limit of the degrees of non-morbid malodorousness may be selected to correspond to any value higher than 2.0 ppm of methyl mercaptan. If it is determined at step B20 in FIG. 13 that the voltage $V_{OUT}$ is lower than the third reference value $V_3$, an instruction signal may be issued from the central processing unit 112 to turn on the fifth indicator 110e of the device to illuminate or flicker at step B15 as in the routine program shown in FIGS. 12A and 12B. When it is determined at step B20 in FIG. 13 that the voltage $V_{OUT}$ is higher than the third reference value $V_3$, an instruction signal may be issued as at step B21 to turn on the sixth indicator 110f of the device to illuminate or flicker. The illumination or flickering of the sixth indicator 110f is thus indicative of the fact that the data represented by the voltage $V_{OUT}$ is presumed to have resulted simply from the eating of fish and/or garlic and/or the drinking of an alcoholic beverage and accordingly that the subject under examination is in a physical condition not qualified for testing. If it is found that the voltage $V_{OUT}$ is not higher than the third reference value, an instruction signal is issued from the central processing unit 112 as at step B16 to turn on the fifth indicator 110e of the device to illuminate or flicker.

FIG. 14 shows the details of the forced air discharge subroutine to be executed additionally to the routine program hereinbefore described with reference to FIGS. 12A and 12B to scavenge the sensor chamber 80 in the device shown in FIGS. 7A to 7C. The forced air discharge subroutine may be executed subsequently to the step B19 at which any of the indicators 110c to 110e is turned off. Subsequently to the step B19 or to the preceding step 18, a fan start flag $F_{fs}$ of logic "1" state is output from the central processing unit 112 at an initial step C01 of the air discharge subroutine. In response to this fan start flag $F_{fs}$ of logic "1" state, an instruction signal is issued from the central processing unit 112 to start the fan-drive motor 94 for the air discharge fan 92 with a control signal supplied to the driver circuit 132 from the output buffer 126 of the control circuit 28 shown in FIG. 8. The step C01 is followed by step C02 at which an instruction signal is issued from the central processing unit 112 to start the timer "F" incorporated in the control circuit 28. The timer "F" is set for a period of time predetermined for which the fan 92 is to be in operation for purging air out of the sensor chamber 80. When it is confirmed at step C03 that the time set by the timer "F" has lapsed, the central processing unit 112 shifts the fan start flag $F_{fs}$ to logic "0" state to stop the fan-drive motor 94 as at step C04. After the fan drive motor 94 is thus brought to a stop, the routine program including the forced air discharge subroutine reverts to step B02 and may repeat the steps B02 to B19 of the routine program hereinbefore described with reference to FIGS. 12A and 12B.

FIGS. 15A to 15D are flowcharts showing the details of the routine program illustrated in FIG. 11C. The routine program herein shown is applied to the device shown in FIGS. 9A and 9B and is to be executed by the central processing unit 112 included in the control circuit 28 shown in FIG. 10. The routine program starts with the power supply switch 42 closed manually and first proceeds to step D01 to initialize the central processing unit 112 and RAM unit 122 of the control circuit 28 to set up various operational parameters and modes of operation in accordance with prescribed default rules. At this step D01, the number N to indicate the number of times of the test cycles to be repeated for the testing operation is set at three in accordance with the default rules. The step D01 is followed by step D02 at which an instruction signal is issued from the central processing unit 112 to indicate on the message display section 138c of the display screen 138 a message reading "PLEASE WAIT" to request the subject to wait until the device is ready to accept his exhalation.

The step D02 is followed by step D03 at which a control signal is issued from the input/output buffer 176 to the switch circuit 36 to select the sensor cleaning voltage $V_{CL}$ as an input to the heater element 24. With the sensor cleaning voltage $V_{CL}$ thus applied to the heater element 24, the sensor element 20a is heated to a temperature of typically 420° C. and is cleared of the contaminants which may have been left thereon after the latest use of the detector device. Upon termination of the sensor cleaning step D03, an instruction signal is issued from the central processing unit 112 as at step D04 to start the timer "A" incorporated in the control circuit 28. The timer "A" is set for a period of time predetermined for the cleaning of the sensor element 20a. When it is confirmed at a decision step D05 that the time set by the timer "A" has lapsed, a control signal is issued from the input/output buffer 176 to the switch circuit 36 to shift the input voltage for the heater element 24 from the sensor cleaning voltage $V_{CL}$ to the heater voltage $V_H$ as at step D06.

It is then confirmed at decision step D07 whether or not the voltage applied to the sensor element 20a is correctly of the predetermined bias level $V_B$. If it is found at this step D07 that the voltage applied to the sensor element 20a is higher or lower the level $V_B$, the central processing unit 112 issues an instruction signal at step D08 to indicate on the message display section 138c of the display screen 138 a message reading "ADJUST VOLTAGE" to request the subject or operator to adjust the sensor voltages through manipulation of the voltage adjustment wheel 150. The voltage adjustment wheel 90 will be then manipulated by the subject or operator to continuously vary the voltage across the variable resistor 48 and accordingly each of the bias, heater and sensor cleaning voltages $V_B$, $V_H$ and $V_{CL}$ to be used in the detector device. When it is confirmed at step D09 that the voltage applied to the sensor element 20a has been correctly adjusted to the level $V_B$, an instruction signal is issued at step D10 to clear the message currently appearing on the display section 138c. If it is found at step D09 that the voltage applied to the sensor element 20a has not been correctly adjusted to the level $V_B$, the central processing unit 112 waits until the adjustment of the voltage to the proper level is made by the operator. At the step D08 may be further displayed the detected value of the bias voltage $V_B$ either numerically or graphically on any section of the display screen 138.

Subsequently to the step D10 or when it is found at the step D07 that the voltage applied to the sensor element 20a is correctly of the level $V_B$, the central processing unit 112 issues an instruction signal at step D11 (FIG. 15B) to indicate on the message display section 138c of the display screen 138 messages reading "READY" and "START TEST" to request the subject or operator to depress the test start key 140 on the control panel 136. After these messages are indicated on the display section 138c, it is confirmed at step D12 whether or not there is a signal produced with the test start key 140 depressed and the associated switch 140' closed. When it is confirmed that there is such a signal produced and supplied to the control circuit 28, a test start flag $F_{ts}$ of logic "1" state is output from the central processing unit 112 as at step D13. Where the fan-drive motor 162 is of the reversible type as previously noted, the step D13 is followed by step D14 at which a suction start flag $F_{subroutine}$ of logic "1" state is output from the central processing unit 112. In response to this suction start flag $F_{ss}$ of logic "1" state, the motor 162 is actuated to operate in reverse direction allowing the air discharge fan 160 to operate as a suction fan to produce a suction in the blow-in tube 156. In this instance, an appropriate control signal is supplied to the driver circuit 180 from the input/output buffer 176 of the control circuit 28 shown in FIG. 10.

In response to this test start flag $F_{ts}$ of logic "1" state, an instruction signal is issued from the central processing unit 112 as st step D15 to indicate on the message display section 138c of the display screen 138 a message reading "PLEASE BLOW" to request the subject to blow into the device through the blow-in tube 156 so that the air exhaled by the subject is admitted into the sensor chamber 154 with the aid of the suction induced in the tube 156. After the message "PLEASE BLOW" is indicated on the display section 138c at step D15, an instruction signal is issued from the central processing unit 112 at step D16 to start the timer "B" in the control circuit 28. The timer "B" is set for a period of time predetermined to allow the subject to have time sufficient to blow into the sensor chamber 154. When it is confirmed at step D17 that the time set by the timer "B" has lapsed, the central processing unit 112 shifts each of the test start flag $F_{ts}$ and suction start flag $F_{ss}$ to logic "0" state as at step D18.

The air exhaled by the subject having been admitted into the sensor chamber 150, the voltage $V_{OUT}$ produced across the sensor element 20a is increased to a level which is higher than the bias voltage $V_B$ and which varies with the concentration of the malodorants contained in the air in the chamber 150. Subsequently to the step D18, it is thus detected at a decision step D19 whether or not the voltage $V_{OUT}$ currently present across the sensor element 20a is higher than the bias voltage $V_B$. For the reason previously explained, the voltage $V_{OUT}$ may be compared not with the bias voltage $V_B$ per se but with a voltage slightly higher than the bias voltage $V_B$.

If the subject has blown into the device by the point of time when the step D18 is reached, the answer for the step D11 is given in the affirmative. When it is thus confirmed that voltage $V_{OUT}$ is higher than the bias voltage $V_B$ or than a voltage slightly higher than the bias voltage $V_B$, an instruction signal is issued from the central processing unit 112 as at step D20 to clear the message "PLEASE BLOW" currently appearing on the message display section 138c. Subsequently, the central processing unit 112 calculates the concentration of malodorant gases represented by the currently detected output voltage $V_{OUT}$ of the sensor element 20a as at step D21 (FIG. 15C). The step D21 is followed by a step D22 at which the central processing unit 112 issues an instruction signal to indicate the calculated value $\phi_1$ of the concentration graphically on the graphic display section 138a and numerical data display section 138b of the display screen 138. Furthermore, the calculated value $\phi_1$ is stored as the first test data into the RAM unit 122 in the control circuit 28 at step D23. Subsequently, the number N indicating the number of times of the test cycles which have been repeated after the central processing unit 112 and RAM unit 120 were initialized at step D01 is decremented by one at a subsequent step D24.

After the first test data representative of the result of the first cycle of testing operation is stored into the central memory unit 122, the central processing unit 112 issues an instruction signal at step D25 to indicate on the message display section 138c of the display screen 138 a message reading "END TEST" to request the subject or operator to depress the test end key 142 on the control panel 136. After this message is indicated on the display section 138c, it is confirmed at step D26 whether or not there is a signal produced with the test end key 142 depressed and the associated switch 142' closed. When it is confirmed that there is such a signal produced and supplied to the control circuit 28, the central processing unit 112 issues an instruction signal at step D27 to clear the message currently appearing on the display section 138c.

Subsequently to the step D27, it is queried at step D28 whether or not the number N equals zero. During the first cycle of testing operation, the number N decremented at step D24 equals two and for this reason the routine program proceeds from the step D28 to the forced air discharge subroutine A05 shown in FIG. 14. By the forced air discharge subroutine included in the routine program shown in FIGS. 15A to 15D, the fan start flag $F_{fs}$ of logic "1" state is first output from the central processing unit 112 at step C01. In response to this fan start flag $F_{fs}$ of logic "1" state, an instruction signal is issued from the central processing unit 112 to start the fan-drive motor 162 for operation in forward direction with an appropriate control signal supplied to the driver circuit 180 from the input/output buffer 176 of the control circuit 28 shown in FIG. 10. The air discharge fan 160 is now driven to blow fresh air into the sensor chamber 154 so that the air which has been blown into the chamber 154 is forced out of the chamber 154 through the air outlet opening 166 and vent hole 168 (FIG. 9B). The step C01 is followed by step C02 at which an instruction signal is issued from the central processing unit 112 to start the timer "F" in the control circuit 28. When it is confirmed at step C03 that the time set by the timer "F" has lapsed, the central processing unit 112 shifts the fan start flag $F_{fs}$ to logic "0" state to stop the fan drive motor 162 as at step C04.

Figure 15A:
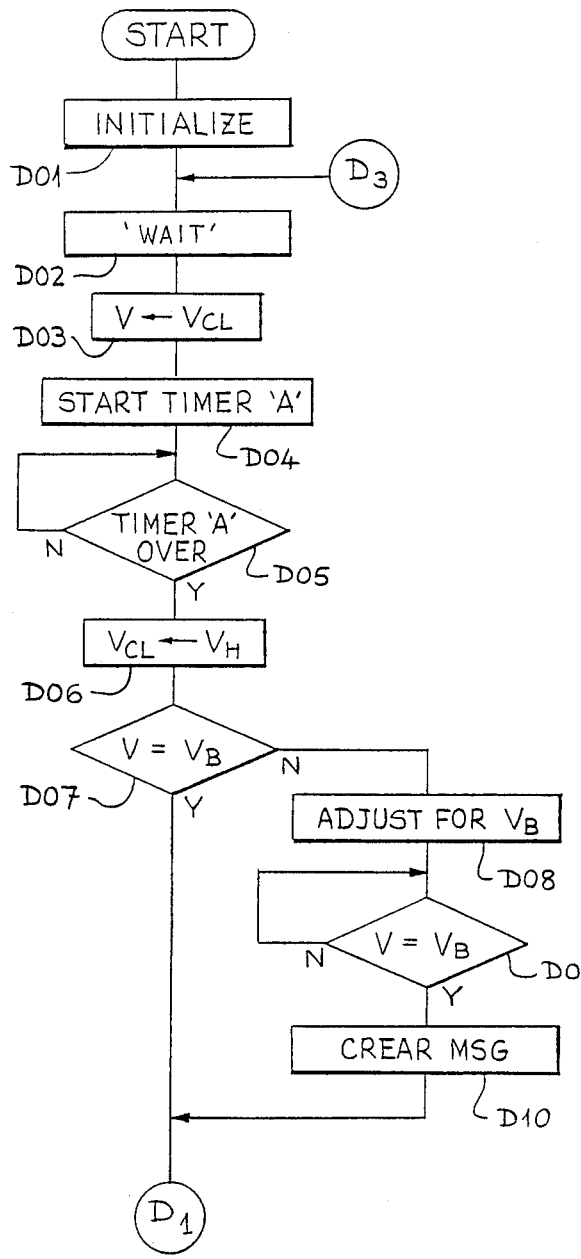
Figure 15B:
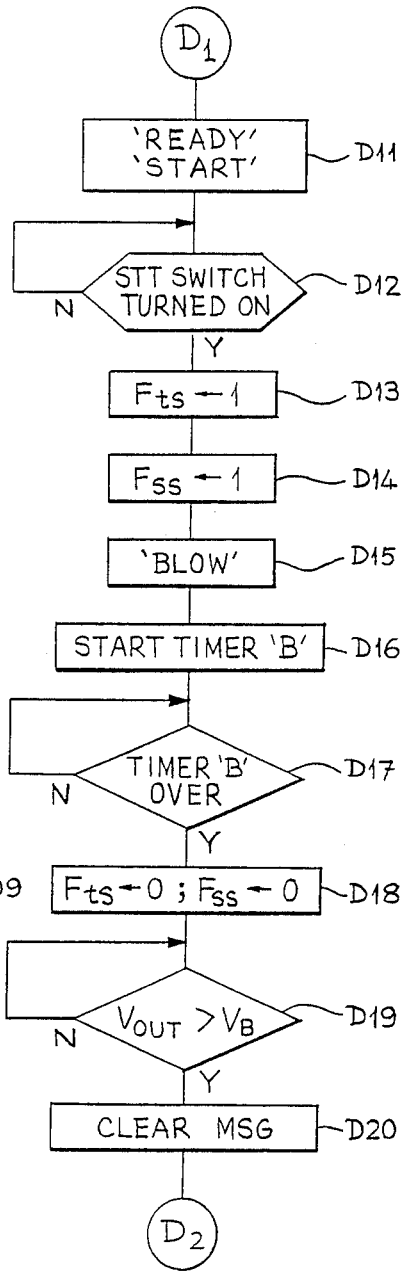

After the fan-drive motor 162 is thus brought to a stop, the routine program reverts to step D02 shown in FIG. 15A to repeat the series of steps D02 to D28 to calculate the value $\phi_2$ of the concentration of malodorant gases detected from the air blown by the subject for a second time. The calculated value $\phi_2$ of the concentration of malodorant gases is indicated on the sections 138a and 138b of the display screen 138 and is stored as the second test data into the RAM unit 122 in the control circuit 28. During this second cycle of testing operation, the number N indicating the number of times of the test cycles which have been repeated is further decremented by one. When it is thereafter confirmed that the test end key 142 is depressed for a second time, the routine program further reverts to the step D02 to repeat the steps D02 to D28 so that the value $\phi_3$ of the detected concentration of malodorant gases is calculated, indicate on the sections 138a and 138b of the display screen 138 and stored as the third test data into the RAM unit 122.

At step D21 in the third cycle of testing operation, the number N indicative of the number of times of the test cycles repeated is finally decremented to zero at step D24. It therefore follows that the answer for the subsequent decision step D28 is given in the affirmative so that the step D28 is followed by a new step D29 at which an instruction signal is issued from the central processing unit 112 to indicate a message reading "PLEASE WAIT" on the message display section 138a of the display screen 138. The central processing unit 112 then fetches the first, second and third test data of the detected concentrations of malodorant gases from the RAM unit 122 and at step D30 calculates the arithmetic mean $\overline{\phi}$ of the values $\phi_1$, $100_2$ and $\phi_3$ represented by the data as. processing unit 112 then issues an instruction signal at a subsequent step D31 whereby the arithmetic mean $\overline{\phi}$ thus calculated is indicated graphically and numerically on the sections 138a and 138b, respectively, of the display screen 138.

Subsequently to step D31, it is detected at step D32 (FIG. 15D) whether or not there is a signal $S_p$ produced with the print request key 148 depressed on the control panel 136. If it is found that there is such a signal $S_p$ input through the switch 148' to the input/output buffer 176, the central processing unit 112 outputs a print start flag $F_{ps}$ of logic "1" state as at step D33. In response to this print start flag $F_{ps}$ of logic "1" state, the values indicating the results of the three cycles of testing operation and the arithmetic means of such values are output in the form of printed information from the printer which may be incorporated within the device. Subsequently to step D33, an instruction signal is issued from the central processing unit 112 at step D34 to start the timer "C" in the control circuit 28. The timer "C" is set for a period of time predetermined to allow the printer to complete its operation. When it is then confirmed at step D35 that the time set by the timer "C" has lapsed, the central processing unit 112 shifts the printer start lag $F_{ps}$ to logic "0" state as at step D36. Thereafter, the routine program reverts to step D01 (FIG. 15A) and may repeat the steps D01 to D36 the routine program hereinbefore described with reference to FIGS. 15A to 15D.

Figure 16:
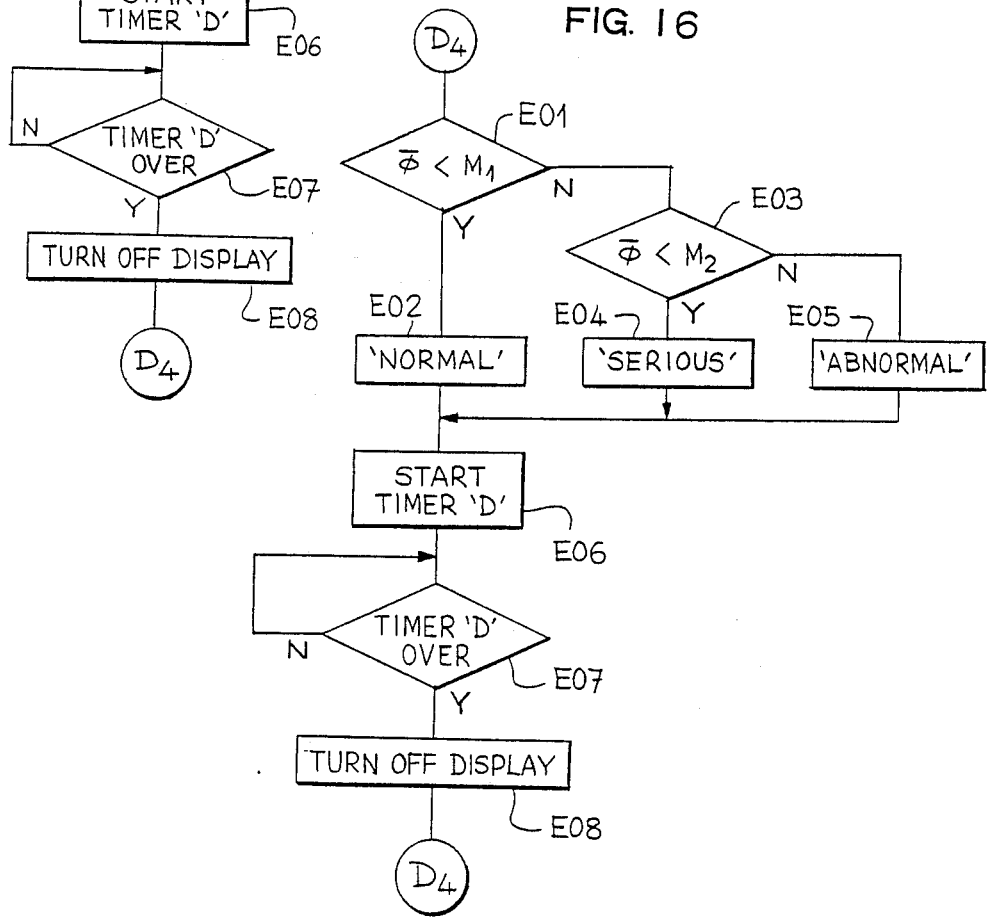
FIG. 16 is a flowchart showing the details of a diagnosis subroutine which is included in the routine program illustrated in FIG. 11D additionally to the routine program of FIG. 11C.

FIG. 16 is a flowchart showing the details of the diagnosis subroutine A08 which forms part of the routine program illustrated in FIG. 11D.

The diagnosis subroutine shown in FIG. 16 is subsequent to the step D31 of the routine program described with reference to FIGS. 15A to 15D and intervenes between the connector D4 bridging the flowcharts of FIGS. 15C and 15D. After the arithmetic mean $\bar{\phi}$ of the values $\phi_1$, $\phi_2$ and $\phi_3$ calculated from the detected concentrations of malodorant gases, it is queried at a decision step E02 whether or not the mean value $\bar{\phi}$ calculated at step D30 (FIG. 15C) is less than a predetermined first reference value $M_1$. This first reference value $M_1$ is representative of the upper limit of the degrees of malodorousness of human exhalations determined to be normal and permissible. When it is determined at step E01 that the mean value $\bar{\phi}$ is less than the first reference value $M_1$, an instruction signal is issued from the central processing unit 112 as at step E02 to indicate a message reading "NORMAL" on the message display section 138c of the display screen 138.

If it is found at step E01 that the mean value $\bar{\phi}$ of the detected concentrations of malodorant gases is not less than the first reference value $M_1$, then it is tested at step E03 whether or not the mean value $\bar{\phi}$ is less than a predetermined second reference value $M_2$. This second reference value $M_2$ is larger than the first reference value $M_1$ and is representative of the upper limit of the degrees of malodorousness of human exhalations determined to be serious and impermissible. When it is determined at step E03 that the mean value $\bar{\phi}$ is less than the second reference value $M_2$, an instruction signal is issued from the central processing unit 112 as at step E04 to indicate a message reading "SERIOUS" on the section 138c of the display screen 138. If it is found at step E03 that the mean value $\bar{\phi}$ is not less than the second reference value $M_2$, then an instruction signal is issued from the central processing unit 112 as at step E05 to indicate a message reading "ABNORMAL" on the section 138c of the display screen 138. The message "ABNORMAL" thus displayed on the section 138c of the display screen 138 is indicative of the fact that the subject's halitosis is of an abnormal degree and that the subject is diagnosed to be suffering from serious ozostomnia.

Subsequently to any of the steps E02, E04 and E05, the routine program proceeds to a step E06 at which an instruction signal is issued from the central processing unit 112 to start the timer "D" (not shown) provided in the control circuit 28 shown in FIG. 8. The timer "D" is set for a period of time for which the message "NORMAL", "SERIOUS" or "ABNORMAL" is to be displayed on the section 138c of the display screen 138. When it is confirmed at step E07 that the time set by the timer "D" has lapsed, an instruction signal is issued from the central processing unit 112 at step E08 to clear the message currently on display, whereupon the routine program proceeds to step D32 in the flowchart of FIG. 15D to carry out the print output subroutine A07 as hereinbefore described with reference to FIG. 15D. In the routine program shown in FIG. 16, the result of diagnosis as displayed at any of the steps E02, E04 and E05 as well as the values indicating the results of the three cycles of testing operation is output in the form of printed information from the printer.

The limits of the permissible and impermissible degrees of malodorousness represented by the first and second reference values $M_1$ and $M_2$, respectively, of the mean value $\bar{\phi}$ of the detected malodorant concentrations may be selected similarly to those used in the routine program described with reference to FIGS. 12A and 12B. Thus, the first and second reference values $M_1$ and $M_2$ of the mean value $\bar{\phi}$ may be selected to correspond to 0.2 ppm and 0.5 ppm, respectively, of methyl mercaptan for the reason explained hereinbefore.

Figure 17:
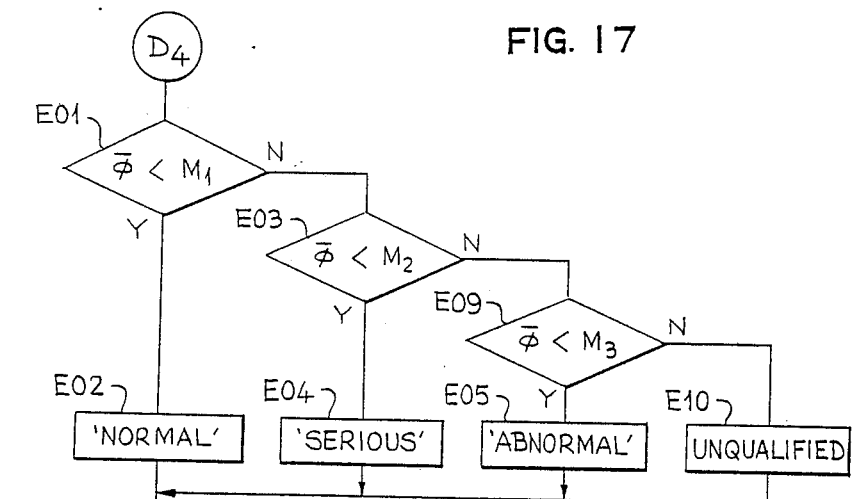
FIG. 17 is a flowchart showing a modification of the diagnosis subroutine illustrated in FIG. 16.

FIG. 17 shows a modification of the diagnosis subroutine hereinbefore described with reference to FIG. 16. When the answer for the step E03 is given in the negative in the subroutine illustrated in FIG. 17, it is questioned at step E09 whether or not the mean value $\phi$ of the detected malodorant concentrations is larger than a predetermined third reference value $M_3$. This third reference value $M_3$ is far larger than the second reference value $M_2$ and is representative of the lower limit of the degrees of malodorousness of human exhalations to result from the eating of fish and/or garlic and/or the drinking of an alcoholic beverage. Such a limit of the degrees of non-morbid malodorousness may be selected to correspond to any value higher than 2.0 ppm of methyl mercaptan as previously noted. When it is determined at step E09 that the mean value $\phi$ of the detected malodorant concentrations is less than the third reference value $M_3$, an instruction signal is issued from the central processing unit 112 as at step E04 to indicate a message reading "SERIOUS" on the section 138c of the display screen 138 as in the subroutine shown in FIG. 16. If it is found at the additional decision step E09 that the mean value $\phi$ is larger than the third reference value $M_3$, then an instruction signal is issued from the central processing unit 112 as at step E10 to indicate a message reading "UNQUALIFIED CASE" on the section 138c of the display screen 138. The message "UNQUALIFIED CASE" thus displayed on the section 138c of the display screen 138 is indicative of the fact that the data represented by the mean value $\bar{\phi}$ is presumed to have resulted simply from the eating of fish and/or garlic and/or the drinking of an alcoholic beverage and accordingly that the subject under examination is in a physical condition not qualified for testing.

In the routine program described with reference to FIGS. 12A and 12B or in the routine program described with reference to FIGS. 15A to 15D, the first and second reference values of 0.2 ppm and 0.7 in terms of the concentration of methyl mercaptan may be varied by preference. Particularly, the value to be used for the decision of abnormal halitosis may be selected at, for example, 0.7 ppm in terms of the concentration of methyl mercaptan in consideration of the fact that the concentration of methyl mercaptan ranges from about 0.2 ppm to about 0.7 ppm in the exhalations of patients suffering from morbid ozostomnia. Alternatively, the degree of seriousness of halitosis may be determined more minutely in three or more steps. For this purpose, the degree of seriousness of halitosis may be regarded as normal for a concentration lower than 0.2 ppm, as serious but permissible for a concentration between 0.2 ppm and 0.5 ppm, as serious and impermissible but not abnormal for a concentration between 0.5 ppm and 0.7 ppm, and as abnormal for a concentration higher than 0.7 ppm each in terms of the concentration of methyl mercaptan.

What is claimed is:

1. A halitosis detector device for testing human exhalation for halitosis, comprising
   (a) a chamber having an air inlet through which the exhalation to be tested is to be admitted into said chamber and an air outlet through which the exhalation tested is to be discharged from said chamber,
   (b) sensing means located in said chamber and, when thermally activated, sensitive to malodorant gases including those of predetermined chemical compositions for producing an electrical signal variable in magnitude with the detected concentration of said malodorant gases,
   (c) means which, when electrically activated, is operative to heat said sensing means,
   (d) control means responsive to said signal for determining the degree of malodorousness on the basis of said signal and producing an electric signal representative of the degree of malodorousness determined, and
   (e) display means responsive to the signal from said control means for displaying information relating to the degree of malodorousness represented by the signal from said control means.

2. A halitosis detector device for testing human exhalation for halitosis, comprising
   (a) a chamber having an air inlet through which the exhalation to be tested is to be admitted into said chamber and an air outlet through which the exhalation tested is to be discharged from said chamber,
   (b) sensing means located in said chamber and, when heated to a predetermined first temperature, sensitive to malodorant gases including those of predetermined chemical compositions for producing an electrical signal variable in magnitude with the detected concentration of said malodorant gases,
   (c) means which, when electrically activated, is operative to heat said sensing means selectively to said first temperature or a predetermined second temperature, said second temperature being higher than said first temperature and being selected to regenerate said sensing means,
   (d) control means responsive to said signal for determining the degree of malodorousness on the basis of said signal and producing an electric signal representative of the degree of malodorousness determined, and
   (e) display means responsive to the signal from said control means for displaying information relating to the degree of malodorousness represented by the signal from said control means.

3. A halitosis detector device as set forth in claim 2, in which said display means comprises at least three electrically activated indicators and in which said control means comprises comparing means for comparing said signal from said sensing means with at least two different predetermined reference values, said control means further comprising means operative to selectively activate any one of said indicators depending on the relationship between said signal from said sensing means and each of said reference values.

4. A halitosis detector device as set forth in claim 2, in which said display means comprises at least three message indicating means and in which said control means comprises comparing means for comparing said signal from said sensing means with at least two different predetermined reference values, said control means being operative to selectively activate any one of said message indicating means depending on the relationship between said signal from said sensing means and each of said reference values.

* * * * *